United States Patent
Shalaby

(12) 
(10) Patent No.: US 6,413,539 B1
(45) Date of Patent: Jul. 2, 2002

(54) HYDROGEL-FORMING, SELF-SOLVATING ABSORBABLE POLYESTER COPOLYMERS, AND METHODS FOR USE THEREOF

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

(21) Appl. No.: 09/016,439

(22) Filed: Jan. 29, 1998

Related U.S. Application Data

(63) Continuation-in-part of application No. 08/740,646, filed on Oct. 31, 1996, now Pat. No. 5,714,159.

(51) Int. Cl.[7] .................................................. A61F 2/00
(52) U.S. Cl. ........................ 424/426; 528/272; 528/275; 528/354; 528/361; 525/439; 525/450; 424/78.03; 424/78.06; 424/425; 424/457; 424/462; 424/486; 514/506
(58) Field of Search ............................... 528/272, 275, 528/354, 361; 525/439, 450; 424/425, 426, 457, 462, 486, 78.03, 78.06; 514/506

(56) References Cited

U.S. PATENT DOCUMENTS

| | | |
|---|---|---|
| 3,991,766 A | 11/1976 | Schmitt et al. |
| 4,141,973 A | 2/1979 | Balazs |
| 4,209,607 A | 6/1980 | Shalaby et al. |
| 4,226,243 A | 10/1980 | Shalaby et al. |
| 4,369,229 A | 1/1983 | Shah |
| 4,532,134 A | 7/1985 | Malette et al. |
| 4,911,926 A | 3/1990 | Henry et al. |
| 4,919,939 A | 4/1990 | Baker |
| 4,938,763 A | 7/1990 | Dunn et al. |
| 4,994,277 A | 2/1991 | Higham et al. |
| 5,011,692 A | 4/1991 | Fujioka et al. |
| 5,077,049 A | 12/1991 | Dunn et al. |
| 5,093,319 A | 3/1992 | Higham et al. |
| 5,135,752 A | 8/1992 | Snipes |
| 5,171,148 A | 12/1992 | Wasserman et al. |
| 5,198,220 A | 3/1993 | Damani |
| 5,278,201 A | 1/1994 | Dunn et al. |
| 5,366,733 A | 11/1994 | Brizzolara et al. |
| 5,366,756 A | 11/1994 | Chesterfield et al. |
| 5,385,738 A | 1/1995 | Yamahira et al. |

FOREIGN PATENT DOCUMENTS

| | | |
|---|---|---|
| EP | 0 092 918 | 11/1983 |
| EP | 0 166 596 | 1/1986 |
| EP | 0 636 378 | 2/1995 |
| EP | 0 737 703 A2 | 10/1996 |
| WO | WO 95/03357 | 2/1995 |
| WO | WO 95/35097 | 12/1995 |

*Primary Examiner*—Samuel A. Acquah
(74) *Attorney, Agent, or Firm*—Nixon Peabody LLP

(57) ABSTRACT

The present invention provides novel hydrogel-forming, self-solvating, absorbable polyester copolymers capable of selective, segmental association into compliant hydrogels upon contacting an aqueous environment. Methods of using the novel polyester copolymers of the invention in humans are also disclosed for providing a protective barrier to prevent post-surgical adhesion, treatment of defects in conduits such as blood vessels, and controlled release of a biologically active agent for modulating cellular events such as wound healing and tissue regeneration or therapeutic treatment of diseases such as infection of the periodontium, dry socket, bone, skin, vaginal, and nail infections.

55 Claims, No Drawings

HYDROGEL-FORMING, SELF-SOLVATING ABSORBABLE POLYESTER COPOLYMERS, AND METHODS FOR USE THEREOF

This is a continuation-in-part of U.S. patent application Ser. No. 08/740,646, filed Oct. 31, 1996 now U.S. Pat. No. 5,714,159, which is hereby incorporated by reference.

FIELD OF INVENTION

This invention relates generally to biomedical and/or pharmaceutical applications of absorbable or biodegradable polymeric hydrogels. More particularly, the present invention relates to hydrogel-forming, self-solvating, absorbable polyester copolymers capable of selective, segmental association into compliant hydrogels upon contacting an aqueous environment. The invention also discloses methods of using the polyester copolymers of the invention in humans for providing a protective barrier to prevent post-surgical adhesion, a carrier of viable cells or living tissue, treatment of defects in conduits such as blood vessels, and controlled release of a biologically active agent for modulating cellular events such as wound healing and tissue regeneration or therapeutic treatment of diseases such as cancer and infection of the periodontium, eye, dry socket, bone, skin, vaginal, and nail infections.

BACKGROUND OF THE INVENTION

Hydrogels are materials which absorb solvents (such as water), undergo rapid swelling without discernible dissolution, and maintain three-dimensional networks capable of reversible deformation (Park, et al., *Biodegradable Hydrogels for Drug Delivery,* Technomic Publishing Co., Lancaster, Pa., 1993; W. Shalaby et al., *J. Controlled Rel.,* 19, 131, 1992; and Silberberg, in *Molecular Basis of Polymer Networks* (Baumgartner, A. & Picot, C. E., Eds.), Spring-Verlag, Berlin, 1989, p. 147).

Covalently crosslinked networks of hydrophilic polymers, including water-soluble polymers are traditionally denoted as hydrogels (or aquagels) in their hydrated state. Hydrogels have been prepared to be based on crosslinked polymeric chains of methoxy poly(ethylene glycol) monomethacrylate having variable lengths of the polyoxyethylene side chains, and their interaction as hydrogels, with blood components have been studied (Nagaoka, et al., in *Polymers as Biomaterials* (Shalaby, S. W., et al., Eds.), Plenum Press, 1983, p. 381). A number of aqueous hydrogels (aquagels) have been used in various biomedical applications, such as, for example, soft contact lenses, wound management, and drug delivery. However, methods used in the preparation of these hydrogels, and their conversion to useful articles, are subject to the constraints associated with the nature of their three-dimensional thermosetting structures and, hence, deprive the users from applying the facile processing techniques employed in the production of non-crosslinked thermoplastic materials.

This, and the low mechanical strength of the hydrated networks, led a number of investigators to explore the concept of combining hydrophilic and hydrophobic polymeric components in block (Okano, et al., *J. Biomed. Mat. Research,* 15, 393, 1981), or graft copolymeric structures (Onishi, et al., in *Contemporary Topics in Polymer Science,* (W. J. Bailey & T. Tsuruta, eds.), Plenum Publ. Co., New York, 1984, p. 149), and blends (Shah, *Polymer,* 28, 1212, 1987; and U.S. Pat. No. 4,369,229) to form the "hydrophobic-hydrophilic" domain systems, which are suited for thermoplastic processing (Shah, Chap. 30, in *Water Soluble Polymers* (S. W. Shalaby, et al., Eds.), Vol. 467, ACS-Symp. Ser., Amer. Chem. Soc., Washington, 1991). The "hydrophobic-hydrophilic" domain system (HHDS) undergoes morphological changes which are associated with the hydration of the hydrophilic domains and formation of pseudo-crosslinks via the hydrophobic component of the system (Shah, 1991, cited above). Such morphology was considered to be responsible for the enhanced biocompatibility and superior mechanical strength of the two-phase HHDS as compared to those of covalently crosslinked, hydrophilic polymers. The mechanism of gel formation in the present invention parallels that described by Shah, 1991, cited above, for non-absorbable blends of hydrophilic-hydrophobic domain systems (HHDS). However, differences exist between the copolymers of the present invention, and more particularly, Component "A", and HHDS. In this regard, Component A is based on a water-soluble and water-insoluble block structure (SIBS). This is not a mere physical mixture of two polymers as are the blends described by Shah, 1991, cited above. Additionally, due to the presence of covalent links between the blocks of SIBS, the resulting hydrogel displays higher elasticity compliance and tensile strength while being absorbable. In fact, the SIBS systems are, in some respects, analogous to thermoreversible gels (Shalaby, in *Water-Soluble Polymers,* (Shalaby, S. W., et al., Eds.), Vol. 467, Chapt. 33, ACS Symp. Ser., Amer. Chem. Soc., Washington, DC, 1991a) in displaying a hydration-dehydration equilibrium governing the system transformation, i.e., the gel/liquid equilibrium is driven by the water content of the SIBS. Thus, in the absence of water, the polyoxyalkylene blocks undergo intermolecular segmental mixing with the neighboring hydrophobic blocks to produce a viscous liquid. In the presence of water, competition between the water as an extrinsic solvent and the polyester block for the polyoxyalkylene (POA) block forces the hydration of the POA, and aggregation or association of the polyester blocks to establish pseudo-crosslinks which maintain a 3-dimensional integrity. Since gel formation takes place in an aqueous environment, the POA block will preferentially migrate to the exterior of the gel and interface with the adjoining tissues to establish an adhesive joint, which prevents gel migration from target site and sustains its intended efficacy. As for example, for periodontal and dry socket applications, post-surgical adhesion prevention and treatment of vaginal and bone infections, and other applications where predictable site residence of the gel cannot be compromised.

Synthesis and biomedical and pharmaceutical applications of absorbable or biodegradable hydrogels based on covalently crosslinked networks comprising polypeptide or polyester components as the enzymatically or hydrolytically labile components, respectively, have been described by a number of researchers (Jarrett, et. al., *Trans. Soc. Biomater.,* Vol. XVIII, 182, 1995; Pathak, et. al., *Macromolecules,* 26, 581, 1993; Park, et. al., *Biodegradable Hydrogels for Drug Delivery,* Technomic Publishing Co., Lancaster, Pa., 1993; Park, Biomaterials, 9, 435, 1988; and W. Shalaby, et. al., 1992, cited elsewhere herein). The hydrogels most often cited in the literature are those made of water-soluble polymers, such as polyvinyl pyrrolidone, which have been crosslinked with naturally derived biodegradable components such as those based on albumin (Park, et. al., 1993, cited elsewhere herein; and W. Shalaby, et. al., 1992, cited elsewhere herein). Totally synthetic hydrogels which have been studied for controlled drug release and membranes for the treatment of post-surgical adhesion are based on covalent networks formed by the addition polymerization of acrylic-terminated, water-soluble chains of polyether dl-polylactide block copolymers (Jarrett, et. al., 1995, cited elsewhere herein; and Pathak, et al., 1993, cited elsewhere herein).

Polymer solutions which undergo reversible gelation by heating or cooling about certain temperatures (lower critical solution temperature, LCST) are known as thermoreversible gels. Theoretical and practical aspects of key forms of thermoreversible gels are described by Shalaby, 1991a, cited elsewhere herein. Among the thermoreversible gels discussed by Shalaby are those of amorphous N-substituted acrylamides in water and amorphous polystyrene and crystalline poly(4-methyl pentene) in organic solvents. Prevailing gel formation mechanisms include molecular clustering of amorphous polymers and selective crystallization of mixed phases of crystalline materials. Thermodynamic parameters (enthalpy and entropy) which favor gel formation in terms of LCST are discussed by Shalaby only with respect to the solvent-polymer interaction. Shalaby fails, however, to address self-solvating chains.

U.S. Pat. No. 4,911,926, discloses aqueous and non-aqueous compositions comprised of block polyoxyalkylene copolymers that form gels in the biologic environment, for preventing post-surgical adhesion. Other gel forming compositions for use in preventing post-surgical adhesion include: (a) chitin derivatives (U.S. Pat. No. 5,093,319); (b) aqueous solutions of xanthan gum (U.S. Pat. No. 4,994,277); (c) chitosan-coagulum (U.S. Pat. No. 4,532,134); and (d) hyaluronic acid (U.S. Pat. No. 4,141,973).

Absorbable polymers, or often referred to as biodegradable polymers, have been used clinically in sutures and allied surgical augmentation devices to eliminate the need for a second surgical procedure to remove functionally equivalent non-absorbable devices (U.S. Pat. No. 3,991,766, to Schmitt et al.; and Shalaby, in *Encyclopedia of Pharmaceutical Technology* (J. C. Boylan & J. Swarbrick, eds.), Vol. 1, Dekker, New York, 1988, p. 465). Although these devices were designed for repairing soft tissues, interest in using such transient systems, with or without biologically active components, in dental and orthopedic applications has grown significantly over the past few years. Such applications are disclosed in Bhatia, et. al., *J. Biomater. Sci.,* Polym. Ed., 6(5), 435, 1994; U.S. Pat. No. 5,198,220, to Damani; U.S. Pat. No. 5,198,220, to Wasserman, et. al.; and U.S. Pat. No. 3,991,766, to Schmitt et al.

U.S. Pat. No. 3,991,766, to Schmitt et al., discloses absorbable articles made of polyglycolide, such as sutures, clips and storage pallets having medicaments incorporated therein and can be used for both their own mechanical properties and delayed release systems of medicaments. U.S. Pat. No. 5,171,148, to Wasserman et al., discloses the use of absorbable polymers made from p-dioxanone or L-lactide and glycolide as dental inserts for the treatment of periodontal disease. Here, a semiporous mesh material with sealed edges is emplaced between the tooth and gingiva. The implant is attached to the tooth by an absorbable ligature material. U.S. Pat. No. 5,198,220, to Damani, discloses the treatment of periodontal disease through the use of a sustained release composition/device comprising bioactive agents. The composition/device is in a liquid, semi-solid or solid form suitable for insertion into or around the periodontal pocket. Damani also teaches the formation of a gel, or paste, composition consisting of poly(lactyl-co-glycolide) in an acceptable solvent (such as propylene carbonate), with or without propylene and/or polyethylene glycol, and an antibiotic agent such as tetracycline hydrochloride.

Other in-situ forming biodegradable implants and methods of forming them are described in U.S. Pat. Nos. 5,278, 201 ('201 Patent) and 5,077,049 ('049 Patent), to Dunn et al. The Dunn et al., patents disclose methods for assisting the restoration of periodontal tissue in a periodontal pocket and for retarding migration of epithelial cells along the root surface of a booth. The '049 Patent discloses methods which involve placement of an in-situ forming biodegradable barrier adjacent to the surface of the tooth. The barrier is microporous and includes pores of defined size and can include biologically active agents. The barrier formation is achieved by placing a liquid solution of a biodegradable polymer, such as poly(dl-lactide-co-glycolide) water-coagulatable, thermoplastic in a water miscible, non-toxic organic solvent such as N-methyl pyrrolidone (i.e., to achieve a typical polymer concentration of $\leq 50\%$) into the periodontal pocket. The organic solvent dissipates into the periodontal fluids and the biodegradable, water coagulatable polymer forms an in-situ solid biodegradable implant. The dissipation of solvent creates pores within the solid biodegradable implant to promote cell ingrowth. The '859 Patent likewise discloses methods for the same indications involving the formation of the biodegradable barrier from a liquid mixture of a biodegradable, curable thermosetting prepolymer, curing agent and water-soluble material such as salt, sugar, and water-soluble polymer. The curable thermosetting prepolymer is described as an acrylic-ester terminated absorbable polymer.

The '049 and '859 Patents, as well as U.S. Pat. No. 4,938,763 to Dunn et al., disclose polymer compositions primarily consisting of absorbable thermoplastic or thermosetting polymer, dissolved in organic solvent. These compositions are also described to produce, in an aqueous environment, solids which can be used as tissue barrier (Fujita, et. al., *Trans. Soc. Biomater.,* Vol. XVII, 384, 1994) substrate for tissue generation (Dunn, et. al., *Poly. Prepr.,* 35(2), 437, 1994a) or carrier for the controlled delivery of drugs (Sherman, et. al., *Pharm. Res.,* 11(10 5–318, 1994). Acrylate-endcapped poly(caprolactone) prepolymer was also used as a branched precursor for the in-situ formation of a crosslinked system for potential use in controlled drug release (Moore, et. al., *Trans. Soc. Biomater.,* Vol. XVIII, 186, 1995).

A number of controlled delivery systems for the treatment of periodontal disease are also described in the literature. For example, U.S. Pat. No. 4,919,939, to Baker, discloses a controlled release delivery system for placement in the periodontal pocket, gingival sulcus, tooth socket, wound or other cavity within the mouth. The system incorporates microparticles in fluid medium and is effective in the environment of use for up to 30 days. The drug, in 10–50 micron polymer particles, is released at a controlled rate by a combination of diffusion of the drug through the polymer and erosion of the polymer.

U.S. Pat. No. 5,135,752, to Snipes, discloses a buccal dosage form, which melts in the oral cavity, yet will not spontaneously deform at higher temperatures encountered in shipment and storage. This composition comprises two grades of polyethylene glycol, polyethylene oxide, long-chain saturated fatty acid, and colloidal silica.

U.S. Pat. No. 5,366,733, to Brizzolars et al., discloses an oral composition for the local administration of a therapeutic agent to a periodontal pocket comprising at least one therapeutic agent dispersed in a matrix including a biocompatible and/or biodegradable polymer. The composition is administered as a plurality of dry discrete microparticles, said microparticles are prepared by a phase separation process. An oral composition is also described wherein the polymer comprises a block copolymer of polyglycolide, trimethylene carbonate and polyethylene oxide. Apparatus and methods are also provided for dispensing the dry microparticles to the periodontal pocket, whereby they become tacky and adhere to the involved tissue so as to induce long-term therapeutic effects.

In addition, a number of systems for the controlled delivery of biologically active compounds to a variety of sites are disclosed in the literature. For Example, U.S. Pat. No. 5,011,692, to Fujioka et al., discloses a sustained pulsewise release pharmaceutical preparation which comprises drug-containing polymeric material layers. The polymeric material layers contain the drug only in a slight amount, or free of the drug. The entire surface extends in a direction perpendicular to the layer plane and is coated with a polymeric material which is insoluble in water. These types of pulsewise-release pharmaceutical dosages are suitable for embedding beneath the skin.

U.S. Pat. No. 5,366,756, to Chesterfield et al., describes a method for preparing porous bioabsorbable surgical implant materials. The method comprises providing a quantity of particles of bioabsorbable implant material, and coating particles of bioabsorbable implant material with at least one growth factor. The implant can also contain antimicrobial agents.

U.S. Pat. No. 5,385,738, to Yamahira et al., discloses a sustained-release injection system, comprising a suspension of a powder comprised of an active ingredient and a pharmaceutically acceptable biodegradable carrier (e.g., proteins, polysaccharides, and synthetic high molecular weight compounds, preferably collagen, atelo collagen, gelatin, and a mixture thereof) in a viscous solvent (e.g., vegetable oils, polyethylene glycol, propylene glycol, silicone oil, and medium-chain fatty acid triglycerides) for injection. The active ingredient in the pharmaceutical formulation is incorporated into the biodegradable carrier in the following state: (i) the active ingredient is chemically bound to the carrier matrix; (ii) the active ingredient is bound to the carrier matrix by intermolecular action; or (iii) the active ingredient is physically embraced within the carrier matrix.

Furthermore, a common complication which is encountered by many surgeons following tooth extraction is dry socket. Dry socket occurs following three to four percent of routine extractions (Field, et. al., *J. Oral Maxillofac. Surg.*, 23(6), 419, 1985), and its etiology appears to be multifactorial (Westerholm, *Gen. Dent., July–Aug.,* 306, 1988). Over the years, dry socket has been referred to as alveoloalgia, alveolitis sicca dolorosa, avascular socket, localized osteitis, fibrinolytic alveolitis and localized acute alveolar osteomyelitis (Shafer, et al., *A Textbook of Oral Pathology,* 4th Ed., W. B. Saunders Co., Philadelphia, 1974, p. 605, 1974; and Birn, *Int. J. Oral Sureg.,* 2, 211, 1973). Although many chemotherapeutic prevention measures or management have been pursued, none have significantly reduced the incidence of dry socket (Birn, 1973, cited above; Field, et. al., 1985, cited above). Among such approaches to the therapeutic treatment of dry socket, with limited success, are those based on systemic administration of antibiotics (Westerholm, 1988, cited above) or direct placement of powdered sulfadiazine or sulfathiazole into the socket (Elwell, *J. Amer. Dent. Assoc.,* 31, 615, 1944).

To date, the known HHDS and thermoreversible gels can be classified as non-absorbable materials and are expected not to absorb through chain dissociation in the biological environment. Meanwhile, there is a growing interest in developing absorbable sutures and allied surgical devices such as transient implants, which are degraded to bioabsorbable, safe by-products and leave no residual mass at the surgical site, as well as frequently cited clinical advantages (Shalaby, Chap. 3 in *High Technology Fibers* (M. Lewin & J. Preston, eds.), Dekker, New York, 1985; Shalaby, 1988, cited elsewhere herein; Shalaby, *Polym. News,* 16, 238, 1991; Shalaby, *J. Appl. Biomater.,* 3, 73, 1992; Shalaby, *Biomedical Polymers: Designed to Degrade Systems,* Hanser Publ., New York, 1994; and Shalaby, et al, eds. *Polymers of Biological & Biomedical Significance,* Vol. 520, ACS-Symp. Ser., Amer. Chem. Soc., Washington, 1993) have justified the need for novel absorbable hydrogel formulations.

Moreover, such systems as those previously described in the literature, for example, such as by Dunn, et al, (U.S. Pat. No. 4,938,763), teach in-situ formations of biodegradable, microporous, solid implants in a living body through coagulation of a solution of a polymer in an organic solvent such as N-methyl-2-pyrrolidine. However, the use of solvents, including those of low molecular organic ones, facilitates migration of the solution from the application site thereby causing damage to living tissue including cell dehydration and necrosis. Loss of the solvent mass can lead to shrinkage of the coagulum and separation from surrounding tissue.

Furthermore, currently available drug delivery systems deal with solid implants which can elicit mechanical incompatibility and, hence, patient discomfort. The present invention provides novel, hydrogel-forming copolymers, which in contrast to those systems previously described, are absorbable, do not require the use of solvents, and are compliant, swollen, mechanically compatible gels, which adhere to surrounding tissue.

SUMMARY OF THE INVENTION

The primary object of the present invention is to provide a hydrogel-forming, self-solvating, absorbable polyester copolymer capable of selective, segmental association into a compliant hydrogel mass on contact with an aqueous environment.

Another object of the present invention, is to provide such a copolymer optionally comprising a biologically active agent.

Yet another object of the present invention, is to provide such a copolymer optionally comprising a low molecular weight component.

A further object of the present invention, is to provide such a copolymer capable of the controlled-release of a biologically active agent/drug for modulating cellular events, such as, wound healing and tissue regeneration.

A further object of the present invention, is to provide such a copolymer capable of the controlled-release of a biologically active agent/drug for therapeutic treatment of diseases, such as, cancer and infection of the, eye, oral cavity, dry socket, bone, skin, vaginal and nail infections.

A further object of the present invention, is to provide such a copolymer which is capable of being extruded or injected into living tissue, or onto the surface thereof, for providing a protective barrier with or without an anti-inflammatory agent or an agent which inhibits fibrotic tissue production for treating conditions, such as, post-surgical adhesion.

A further object of this invention is to provide such a copolymer for constituting or constructing a carrier of peptides or proteins, vaccines, living cells, or viable tissue for sustaining biological functions both in vitro and in vivo.

A further object of the present invention, is to provide such a copolymer which is capable of acting as a blocking agent or sealant for treating defects in conduits.

Accordingly, the present invention provides hydrogel-forming, self-solvating, absorbable polyester copolymers capable of selective, segmental association into a compliant hydrogel mass on contact with an aqueous environment. In a preferred embodiment of the invention, the copolymer comprises a base component, designated "Component A" herein. As used herein, the terms "Component A" and "copolymer(s)" are interchangeable and refer to the basic structure of the copolymers of the invention. Component A comprises a molecular chain having a hydrophilic block, designated "Y" herein, and a relatively hydrophobic polyester block, designated "X" herein. Hydrophobic block X and hydrophilic block Y more preferably comprises a molecular structure having the following formula: X-Y-X or $(X-Y)_n$, and branched structures thereof. Most preferably, hydrophobic block X comprises a polyester formed by grafting a glycolide, lactide, ε-caprolactone, p-dioxanone, trimethylene carbonate or combinations thereof, onto the hydroxylic or amino groups of a hydrophilic polymer precursor i.e., Y; hydrophilic block Y comprises a polyoxyethylene, poly(oxyethylene-b-oxypropylene), polypeptide polyalkylene oxamate, a polysaccharide, and derivatives thereof; or a liquid, high molecular weight polyether glycol interlinked with an oxalate or succinate functionalities in linear or branched form.

Component A optionally comprises carboxylic end-groups formed by any known technique in the art, such as, for example, end-group succinylation or glutarylation. This facilitates ionically binding a biologically active agent or drug to Component A, such that, drug release can be modulated. The biologically active agent or drug is preferably present on Component A in an insoluble form, such as, (I) a microparticulate dispersion, (2) a surface-deposited coating onto an absorbable microporous microparticles, and/or (3) ionically bound molecules onto the surfaces of absorbable microparticles which are preferably microporous that can be encased in an absorbable polymer to modulated its release further. The encasing can be achieved by allowing a dispersion of active micorpariicle in solution of an absorbable polymer to phase separate by (a) solvent evaporation in with or without emulsion; (b) solvent exchange of nebulized microdroplets onto a precooled organic solvent such as, 2-propanol, which is a non-solvent for the polymer; (c) replacing the non-solvent in (b) with a supercritical fluid; or (d) replacing 2-propanol with a solution of water in an organic solvent.

In another embodiment of the invention, Component A optionally comprises an absorbable carrier associated therewith and, designated "Component B" herein. As used herein, the term "associated therewith" refers to any chemical and/or physical means known in the art for combining components together. The function of Component B is to carry the biologically active agent. This is preferably desirable for medications which call for an initial drug burst and prolonged release thereafter and, thus, highly regulated availability of drugs at the biological site to modulate the release of the bioactive agent bound to component B, the latter may be encased in an absorbable polymer. The encased system can then be used as such for injection in an aqueous dispersion. In a further embodiment of the invention, encased Component B, having a bound bioactive agent such as, a peptide or a protein, is encased in an absorbable polymer as part of an aqueous pharmaceutical formulation for use in parenteral applications.

In a further embodiment of the invention, Component A, with or without component B and/or the biologically active agent, optionally comprises a similarly constituted low molecular weight block copolyester associated therewith. The low molecular weight coplyester preferably is a plasticizer and, more preferably, the plasticizer is designated "Component C" herein.

It is understood that Component A, with or without the biologically active agent/drug and/or compositions of Components A, B, C, the biologically active agent, and variations thereof, can provide a wide range of properties for treating a host of diseases, including, but not limited to, dental, ophthalmic, orthopedic and vascular applications. For example, the copolymers of the invention can: (1) be extruded or injected into living tissue or onto the surface of living tissues to provide a protective barrier to prevent post-surgical adhesion; (2) act as a blocking agent or sealant for treatment of defect in conduits such as blood vessels; (3) facilitate the controlled-release of a biologically active agent/drug for modulating cellular events such as wound healing and tissue regeneration or therapeutic treatment of cancer and diseases such as infection of the periodontium, eye, dry socket, bone, skin, vaginal, and nail infections; (4) facilitate the sustained in vitro or in vivo growth of viable cells and/or living tissues for the purpose of tissue engineering; (5) to aid in wound healing and augmentation; (6) to facilitate hemostasis; (7) to modulate the performance of tissue adhesives; and (8) to the healing of burns and ulcers.

DETAILED DESCRIPTION OF THE INVENTION

The term "Hydrophobic Block(s)" as used herein, refers to absorbable polyester chain block(s) or segment(s) of variable length which, is present in an isolated form, will produce practically amorphous (with less than 5% crystallinity) or totally amorphous material having a $T_g$ of less than 25° C., and preferably, is a viscous liquid at room temperature. Hydrophobic block(s) X comprises copolymeric segments of known chemistries in the art, such as, those comprised from cyclic lactones (e.g., glycolide, l-lactide, dl-lactide, ε-caprolactone, p dioxanone, trimethylene carbonate), polyalkylene oxalate, and the like, as described by Shalaby, 1988, cited elsewhere herein, which disclosure is hereby incorporated by reference. More preferably, hydrophobic segment(s) or block(s) X comprises lactide/glycolide copolymer (with 51 to 80% l- or dl-lactide).

The term "Hydrophilic Block(s)" as used herein, refers to polymeric blocks or segments which, if present in an isolated form, will be water soluble. Hydrophilic block(s) or segment(s) Y comprises poly(oxyethylene), with or without a minor component of a higher homolog, such as, poly (oxypropylene)—polypeptide, polyalkylene oxamate (Shalaby et al., 1980, cited elsewhere herein, which disclosure is hereby incorporated by reference), a polysaccharide, or derivatives thereof. The length of the hydrophilic block and its weight fractions can be varied to modulate the rate of gel formation, its modulus, its water content, diffusivity of bioactive drug through it, its adhesiveness to surrounding tissue, and bioabsorbability.

The term "Hydrogel" or "Hydrogel Mass" as used herein, refers to materials which have a high tendency for water absorption and/or retention, and maintain mechanical integrity through physical crosslinks which are reversible in nature.

The term "Physical Crosslinks" as used herein, refers to a three-dimensional structure which is held together by physical quasi or pseudo crosslinks, or ionic bonds, as compared to covalently crosslinked. These physical crosslinks facilitate the reversibility of the hydrogel. This reversibility property can be influenced by external factors, such as, solvent or heat.

The term "Self-Solvating" as used herein, refers to components of chains which in the absence of external factors i.e., solvents, have greater affinity for physical interaction such that the components are capable of forming a virtually one phase system.

The term "Compliant" as used herein, refers to a material having a low modulus and which is easily deformable.

The term "Biologically Active Agent" as used herein broadly includes any composition or compound of matter which when dispensed in the chosen environment of use produces a predetermined, beneficial and useful result.

The term "Drug" or "Agent" as used herein broadly includes physiologically or pharmacologically active substances for producing a localized effect at the administration site or a systemic effect at a site remote from the administration site.

The term "Plasticizer" as used herein, refers to an absorbable polyester composition with hydrophilic and hydrophobic components similar, or identical to, those of Component A, with the exception of having a higher hydrophilic/hydrophobic ratio in Component C than Component A.

The term "absorbable" means a water insoluble material such as a polymer which undergoes chain disassociation in the biological environment to water soluble by-products.

The term "microparticle" refers to the particles of absorbable polyester, which are preferably in essentially spherical form.

The term "bound microparticle" refers to a microparticle having one or more bioative agent(s)/drug(s), such as, peptide and/or one or more protein ionically immobilized on the microparticle.

The term "encased microparticle" refers to a bound microparticle having a polymer coating, where the polymer coating is not necessarily completely occlusive.

The term "polymer core" is another way of referring to microparticles.

The term "encasing polymer" refers to the polymer that is used to encase a bound microparticle.

The term "gel-forming liquid polyester" refers to materials which absorb solvents such as water, undergo phase transformation and maintain three dimensional networks capable of reversible deformation.

The present invention discloses novel hydrogel-forming, self-solvating, absorbable polyester copolymers, which upon hydration results in a hydrogel mass. The hydrogel mass is stabilized by pseudo-crosslinks provided by a hydrophobic polyester component, such as those comprised from cyclic esters e.g., glycolide, l-lactide, dl-lactide, F-caprolactone, p dioxanone, trimethylene carbonate, polyalkylene oxalate, derivatives thereof and the like, covalently linked to a hydrophilic component comprised of blocks, such as those derived from a polyethylene glycol, polypeptide, polyalkylene oxamate (U.S. Pat. Nos. 4,209,607 and 4,226,243, to Shalaby et al., hereby incorporated by reference), or polysaccharide and derivatives thereof. The polyester copolymers, with or without modifying additives, undergo hydration in the biologic environment leading to selective segmental association thereby forming compliant hydrogels at the application site.

These copolymers are especially useful for localized, controlled delivery of biologically active agents/drugs and protecting or augmenting damaged, compromised, and/or traumatized tissues. More particularly applications of the novel copolymers of the invention include: (a) the treatment of periodontal disease, wherein a tetracycline-, doxycycline- or chlorhexidine-containing hydrogel-former is injected in the periodontal pocket to form an adhesive gel or semi-solid mass in the pocket for the controlled release of such antimicrobial drugs over a period of 2 to 45 days. Near the practical exhaustion of the drug, the polymer will commence to absorb and/or disintegrate substantially as it undergoes advanced stages of degradation; (b) the prevention and treatment of dry socket with formulations similar to those of Component A; (c) providing a hydrogel barrier with or without non-steroidal anti-inflammatory drugs or agents which prohibit fibrotic tissue production on traumatized tissue to prevent post-surgical adhesion; (d) applications as an antimicrobial hydrogel for the treatment of vaginal infections; (e) treatment of bone diseases such as osteomyelitis, with injectable formulations comprising antibiotics including gentamicin and vancomycin; (f) accelerating tissue regenerating in compromised soft and hard tissue, e.g., fractured bone, ulcers, burns, by employing formulations comprising growth promoters, such as growth factors or their oligomeric analogs; and, (g) treatment of diseases such as psoriasis and infected nails using formulations comprising antimicrobial agents. Other applications of the hydrogel-forming copolymers of the invention include (a) blood vessel sealant; (b) vascular blocking agent; (c) carrier for injectable anti-inflammatory formulations in the treatment of joint diseases; (d) active carrier of viable cells or living tissue; (e) carrier for dispensing anti-cancer agents, which may be a peptide or protein or mixtures thereof; (f) hemostatic agent; (g) aid to ligating devices such as surgical staples and sutures; and (h) tissue adhesive.

The copolymers of the invention comprise a primary or base component designated "Component A" herein. Component A comprises molecular chains having a hydrophilic block, designated "Y" herein, and a relatively hydrophobic polyester block, designated "X" herein. The molecular structure of hydrophobic block X and hydrophilic block Y preferably comprises one of the following formulas: X-Y-X or $(X-Y)_n$, and branched structures thereof. More preferably, hydrophobic block X comprises a polyester formed by grafting a glycolide, lactide, $\epsilon$-caprolactone, p-dioxanone, trimethylene carbonate or combinations thereof, onto the hydroxylic or amino-end groups of a hydrophilic polymer precursor i.e., Y. Hydrophilic block Y preferably comprises a polyoxyethylene, poly(oxyethylene-b-oxypropylene), polypeptide, polyalkylene oxamate, a polysaccharide, or derivatives thereof, or a liquid, high molecular weight polyether glycol interlinked with oxalate or succinate functionalities in linear or branched form.

In a preferred embodiment, Component A comprises a polyethylene glycol having a molecular weight of about 400 Daltons which is pre-interlinked with succinate or oxalate bridges to increase the length of the hydrophilic block and, thus, the molecular weight of A without favoring its crystallization. That is, the hydrophilic prepolymer "Y" having hydroxylic end-groups, is end-grafted with a mixture 60/40 dl-lactide/glycolide to produce a block copolymer having a hydrophilic block fraction "Y" of about 0.25. To render Component A more receptive to basic drugs, its end-groups can optionally be carboxylated, for instance, by their acylation with succinic anhydride. Component A, with or without a biologically active agent, is introduced to a biological target site using conventional means and, thereafter, undergoes selective-segmental segregation to form a flexible, compliant, reversible gel which adheres to the surrounding tissues and acquires the configuration of the site. Component A of the invention more preferably comprises an inherent viscosity at 25° C. in chloroform ranging between 0.03 to 0.80 dL/g and can be present as a liquid at room temperature, or practically amorphous material (with less than 5% crystallinity) with a $T_g$ of less than 25° C., which can be extruded through a die or administered through a syringe needle.

Component A comprises copolymeric chains with self-solvating components (analogous to phase mixing of two component miscible blends) to allow its existence as a viscous, extrudable material at room temperature, and its transformation to a flexible reversible hydrogel upon administration to a biological site. These hydrogels adhere tenaciously to adjacent tissues and acquire the shape of the site. The present copolymers are mechanically compatible in highly sensitive sites, as well as, can mediate external mechanical stresses or shocks. As such, the copolymers of the invention can be applied easily without incorporating a major extrinsic water-soluble, potentially cytotoxic organic solvent in order to facilitate upon administration in-situ coagulation to a solid mass.

Component A, with or without a bioactive agent/drug, such as, non-steroidal anti-inflammatory drug (NSAID) or active polypeptide, can be used as a protective barrier, a blocking agent of vascular defects caused by needle puncturing, a sealant of damaged surfaces for preventing post-surgical adhesion or as a carrier of immunostimulants or viable cells. Component A, mixed with an antimicrobial agent/drug, can be injected or applied topically with a suitable known applicator for the treatment of bone, cartilage, nail, skin, and vaginal infections.

In another embodiment of the invention, Component A optionally includes a biologically active agent/drug, such as, an antimicrobial agent, anesthetic agent, antibiotic, and/or a peptide or protein, for regulating cellular events. The biologically active agent/drug can comprise by way of illustration, antifungal agents, antibacterial agents, antibiotics, anti-inflammatory agents, anti-cancer agents, immunosuppressive agents, immunostimulatory agents, dental densitizers, odor masking agents, immune reagents, anesthetics, antiseptics, nutritional agents, antioxidants, lipopolysaccharide complexing agents, prostaglandin analog, cisplatin, peroxides, tissue growth factors, a mixture of any of the foregoing, and the like. The agent/drug can be deposited, wholly or in part, on Component A, with or without carboxy-terminated ends. In an alternative embodiment, the biologically active agent/drug can be deposited, wholly or in part, on a solid carrier, designated "Component B" herein. Component B preferably is an absorbable, powder prior to mixing with Component A. More preferably, Component B is an absorbable, microporous low molecular weight polyester which is highly crystalline and practically insoluble in Component A or, Component B with the active agent, is encased in a less absorbable polymer to modulate the release of the bioactive agent.

A preferred formulation of Components A/B comprises a mixture of 20/80 B/A, with B being a low molecular, microporous polyglycolide with 0.70 to 0.95 solid fraction, average particle size of 0.5–200 micron and carboxyl-bearing chains. High concentration of carboxylic groups on the chains can be achieved by preparing Component B using di- or poly-carboxylic acid as initiators such as malic, citric and tartaric acid. The deposited agent on Component B can exhibit a release profile which can be multiphasic, including: (a) simple, fast diffusion of soluble free drug through gel A; (b) slow diffusion of soluble free drug housed in the pores of B; and, (c) drug release at the surface (both exterior and pore) of B or the chain ends of carboxylated A chains by ion exchange of ionically bound molecules. To modulate the release of active agents, such as amino-acids, peptides or proteins that are bound to Component B, the entire system may be encased in an absorbable polymer, This can be used in conjunction with Component A or a dispersion in an aqueous pharmaceutical formulation for parenteral administration. For anionic drugs, Component B can be chemically modified to reverse its available charge to perform as an anion-exchanger for binding carboxyl-bearing bioactive agents. Similar to the cation-exchanging microparticles, the anion-exchanger can be used in an encased or unencased form in an aqueous dispersion or a non-aqueous gel-former.

By varying the concentration of Component B in Component A, the flow characteristics and release profile of the agent can be modulated. This is important because in certain applications, the flow characteristic or properties of Component A/B formulations can determine the clinical efficacy, particularly in cases of treating periodontal disease, nail infection and bone infection where high viscoelasticity (due to the high weight fraction of the micro-particulate dispersed phase and its physicomechanical interlocking with viscous liquid continuous phase A) of the gel composite is pertinent to assure mechanical stability at the target site.

Component A optionally includes an absorbable low molecular weight component. This component can modulate the rheological properties, gel-formation time, and mechanical disposition of Component A at the target site. The low molecular weight component preferably is a plasticizer and, more preferably, the plasticizer is designated "Component C" herein. Component C can (a) aid the dispersion of Component B in Component A; (b) reduce the overall system viscosity of Component A/B formulation, (c) contribute to reducing the viscosity and facilitating the injectability of Component B if used alone or with a biologically active compound, and/or (d) increase the rate of hydration or gel formation. The absorbable plasticizer, such as Component C, is capable of modulating the viscosity and/or gel-formation rate of Component A, with or without Component B, thereby broadening its applicability. Highly viscous forms of Component A can be easily plasticized with a low molecular weight (inherent viscosity of 0.03–0.15) polyester copolymer Component C, that is made of the same or physically compatible chemical entities as Component A, (but different hydrophilic weight fraction) to produce easily injectable liquid systems.

In a more preferred embodiment, Component A is formed by end-grafting a polyethylene glycol having a molecular weight of about 400–900 Dalton with a mixture of glycolide and l- or dl-lactide in the presence of stannous octoate as a catalyst to produce a block copolymer with (a) ether/ester mass ratios of 20-49/80-51, preferably 25-40/75-55 and, most preferably 30-40/70-60; (b) having an inherent viscosity in chloroform at 25° C. from about 0.03 to 0.80, preferably from about 0.1 to 0.6, more preferably from about 0.15 to 0.5, and most preferably from about 0.2 to 0.4 dL/g; and (c) is in the form of an extrudable, essentially amorphous, semi-solid having a $T_g$ of less than 25° C., preferably an amorphous material having a $T_g$ of less than 37° C., and more preferably a viscous liquid at room temperature that can be easily administered through a syringe needle.

In a still more preferred embodiment, copolymer Component A is formed by end-grafting an oxalate-, succinate- or glutarate-interlinked liquid polyethylene glycol having a molecular weight of more than 1200 Dalton with a mixture of glycolide and l- or dl-lactide in the presence of stannous octoate as a catalyst to produce a block copolymer with (a) ether/ester mass ratio of 20-49/80-51 and preferably 25-40/75-55 but most preferably 30-40/70-60; (b) having an inherent viscosity in chloroform at 25° C. of about 0.03 to 0.80, preferably 0.1 to 0.60, more preferably, 0.15 to 0.50, and most preferably, 0.2 to 0.4 dL/g; and (c) in the form of extrudable, essentially amorphous semi-solid having a $T_g$ of less than 25° C. and preferably an amorphous material having a $T_g$ of less than 25° C. and, more preferably, a viscous liquid at room temperature that can be easily administered through a syringe needle.

Formulations comprised of the polyester-alkylene carbonate copolymers of the invention are suitable carriers of biologically active agents/drugs at typical loading levels of about 0.02 to 20%. The chain of Component A or Component C can be succinylated to provide acidic end-groups for ionic binding of the agents/drugs. Liquid compositions made of Component A or Components A/C, with or without agent/drug, can form hydrogels upon contacting a liquid environment. This is achieved through the hydration of the hydrophilic block of the copolymeric chains leading to intramolecular conformational changes and association of the hydrophobic blocks (or segments) as pseudo-crosslinks in a reversible, hydrophilic/hydrophobic hydrogel system.

For copolymer formulations comprising the agent, such morphology provides a suitable environment for the controlled release of the agent. The agent can be present in a soluble or dispersed form. Preferably, the agent is deposited on a micronized powder, more preferably a microporous absorbable powder and, most preferably, a powder (Component B) which offers an ion-binding, high surface area for ionically immobilizing part of the soluble agent to control its release and, thus, produce copolymers with a multiphasic release profile over a period of 2 to 60 days. To prolong release further for up to 3 or 6 months, the microparticulate with the immobilized active agent may be coated or encased with a slow-absorbing polymer. This may be used in a parenteral aqueous formulation or non-aqueous gel-forming system (e.g., Component A).

More specifically, the biologically active agents can be present as (a) a solute in Component A; (b) a dispersed solid in Component A; (c) a coating on Component B; (d) ionically bound molecules on Components A and/or B; and/or (e) mechanically held within the pores of Component B. Each of these forms of drug will have its own release pathway and, thus, bio-availability at the site. Depending on the concentration of Component B, the hydrogel-forming formulation can be made to have a broad range of properties and gel-formation kinetics to allow its use in many applications.

Component A with a biologically active agent and/or Components B and/or C, is used for treatment of periodontal disease, osteomyalitis, and dry socket. While a discussion follows for using the copolymers of the invention for treatment of periodontal disease, it is understood that this discussion is for purposes of illustration only and, not limitation, and the copolymers of the invention have broad applications of use. Periodontal disease, as used herein, is a general term for a number of diseases that affect the periodontal tissue. These diseases are characterized by a range of symptoms including inflammation, bleeding, exudation of pus from the gingival sulcus, deepening of the sulcus to form periodontal pockets, tissue lesions, loss of connective tissue, alveolar bone loss, and ultimately tooth loosening and loss. The primary cause of periodontal disease is now believed to be bacterial infection of the plaque that forms on tooth surfaces below the gingival margin. The copolymer formulations of the present invention are useful for prolonged, controlled dispensing of a range of drugs and agents, such as, for example: (a) prophylactic prolonged application of minerals and ions, such as calcium or fluoride ion; (b) prolonged controlled exposure to local antiseptics, including, chlorhexidine and tibezonium iodide; (c) controlled antibiotic delivery, including such antibiotics as aminoglycosides, macrolides such as erythromycin, penicillins, cephalosporins and the like; (d) anesthetic/analgesic delivery pre- or post surgery or to treat other mouth pain using such agents as amide-type local anesthetics like lidocaine, mepivacaine, pyrrocaine, bupivacaine, prilocaine, etidocaine, or the like; (e) local controlled delivery of non-steriodal anti-inflammatory drugs such as ketorolac, naproxen, diclofenac sodium and fluribiprofen; and (f) local controlled release antiviral agents (e.g., acyclovir and ganciclovir), immuno-suppressants (e.g., cyclosporin), anti-glaucoma drugs and anti-cancer drugs (interferon and somatostatin analogs). It is recognized that in certain forms of therapy, combinations of agents/drugs in the same delivery system i.e., copolymer of the invention, can be useful in order to obtain an optimal effect. Thus, for example, an antibacterial and an antiinflammatory agent may be combined in a single copolymer to provide combined effectiveness.

It has also been recently shown that regrowth and repair of periodontal connective tissue can be encouraged with the aid of polypeptide mitogenic growth factors. See, for example, V. P. Terranova et al., Biochemically Medicated Periodontal Regeneration, J. Periodont. Res., 22, pages 248–251, incorporated herein by reference. The copolymers of the present invention can be designed to release appropriate encapsulated, or uncapsulated, growth factors, including, epidermal growth factors, human platelet derived TGF-B, endothelial cell growth factors, thymocyte-activating factors, platelet derived growth factors, fibroblast growth factor, fibronectin or laminin.

The drug/agent can be used at a level of from about 0.1% to a about 70%, preferably form about 1% to about 50%, most preferably form about 2% to about 30%. The copolymers of the invention can be designed to release drug to provide a steady state number average concentrations of from about 1 µg to about 2000 µg, preferably form about 20 µg to about 1200 µg, most preferably from about 50 µg to about 800 µg per milliliter of the gingival crevicular fluid of a treated periodontal pocket. The steady state release rates can be altered by varying component ratios of the copolymer formulations. The steady state conditions are preferably used since initial bursts are accounted for as well as delays in release. For example, in the case of a ten (10) day therapy, steady state is generally reached in about one to two days. More preferably, a formulation for treating periodontal disease comprises 20/80 Components B/A, containing 1–3% of an active drug such as chlorhexidine or tetracycline.

In addition to the agent/drug, the copolymer formulations of the present invention can include a variety of optional components. Such components include, but are not limited to, surfactants, viscosity controlling agents, medicinal agents, cell growth modulators, dyes, complexing agents, antioxidants, other polymers such as carboxymethly cellulose, gums such as guar gum, waxes/oils such as castor oil, glycerol, dibutyl phthalate and di(2-ethylhexyl) phthalate as well as man others. If used, such optional components comprise form about 0. 1% to about 20%, preferably from about 0.5% to about 5% of the total copolymer formulation The copolymers of the invention can be inserted into the periodontal pocket or gingival region, and can be administered in the form of a particle, film or sheet. The size, shape and thickness can be changed according to the condition of the disease to be treated. Ordinarily, the size, shape and thickness are changed according to the size of the periodontal pocket of the patient or the condition of the gingiva.

In another embodiment of the invention, there is contemplated pharmaceutical formulations comprising the copolymers of the invention. For example, a preferred pharmaceutical formulation comprises an injectable viscous fluid of Component A, Components A/B, Components A/B/C and/or Components A/C, containing about 0.01% to 10% agent/drug and, more preferably about 0.2% to 5% of agent/drug. The released of the agent/drug is over a period of 1 to 60 days and, more preferably 7 to 45 days. The drug/agent can include anti-microbials, such as, chlorhexidine, tetracycline, doxycycline and metronidazole; antibiotics, such as, gentamicin and vancomycin; and compounds which can accelerate wound healing or tissue regeneration, prevent post-surgical adhesion, neoplastic formation, and prevent or accelerate blood clotting.

In another embodiment of the pharmaceutical formulation, the copolymer comprises part or all of the bioactive agent deposited on a microporous and/or finely divided absorbable powder, such as, those consisting of low molecular weight crystalline polyglycolide or copolyglycolide. The powder is formed by low to moderate conversion (that is 60-95%) ring-opening polymerization of glycolide or a mixture made predominantly of glycolide and small amounts of other lactones. The polymerization is carried out in the presence of stannous octoate as a catalyst and sufficient concentration of glycolic acid as an initiator to produce a mass. Upon quenching, grinding, roll-milling in an inert medium, and extraction with water, 2-propanol, microporous particles are produced having (a) 1 to $200\mu$ diameter and, more preferably 5–75$\mu$; (b) an inherent viscosity in hexafluoro-2-propanol at 25° C. of <0.03 to 0.3 and, more preferably <0.05 to 0.2 dL/g; (c) contain less than 2% residual monomer; and (d) have 0.03 to 0.35 and, more preferably 0.05 to 0.25 pore fraction. For encasing the microparticles with an absorbable polymer, a lactide polymer based on 60 to 100 lactide residues may be used.

In another embodiment, the pharmaceutical formulation consists of Component A with or without Component C and preformed microspheres (or microcapsules) of the bioactive agent/drug in an absorbable polymer.

An important difference between conventional formulations in the art and the novel copolymers of the invention, is that the present copolymers do not include the use of organic solvents. Such solvents can compromise the copolymers shelf-stability, as in the case of a polyester in a basic solvent such as N-methyl-pyrrolidine, which can catalyze chain dissociation in the presence of trace amounts of moisture. The prior art formulations also teach the use of other reactive solvents such as propylene glycol (which degrades the polyester chain through alcoholysis), or trimethylene carbonate (which can copolymerize with the polyester chain). Moreover, should the prior art formulations be radiation sterilized, the presence of a solvent can lead to the generation of new chemical species originating from the solvent as well as in combination with the bioactive ingredient. In effect, organic solvents described in the prior art can compromise the purity and efficacy of both the drug (optional) and polymer which can, in turn, be associated with unsafe use.

Another feature of the novel copolymers of the invention, is that when administered to a biological site the copolymers do not experience discernible reduction in organic mass, as is the case of prior art compositions which coagulate in-situ by leaching out a major water-soluble component. Leaching out a major water-soluble components can be associated with shrinkage and separation from the surrounding tissue and, in some instances, uncontrolled formation of microporous mass. Because the copolymers of the invention are comprised of copolymeric chains, the copolymers can be easily tailored to modulate its viscosity without the intervention of a new chemical species, such as, an organic solvent.

A further feature of the novel copolymers of the invention, is that since the copolymers are comprised of self-solvating molecules, its conversion to a hydrogel about a drug provides a uniform distribution of the therapeutic agent, and thus, more reproducible release profile, in contrast with prior art systems where complex physical events prevail due to the presence of leachable solvents.

A microparticle of the present invention is crystalline and is made of an absorbable polyester, such as polyglycolide having one or more carboxylic groups on the individual chains which results in a sufficient concentration of carboxylic groups on the surface of the microparticle and immediate subsurface of the microparticle to complex and ionically immobilize a peptide(s) and/or a protein(s) having one or more basic groups. Or the carboxylate groups of the polyglycolide can be amidated, for example by a diamine, preferably a primary or secondary amine or a mixture thereof, wherein the amine forms a complex that ionically immobilizes a peptide(s) and/or a protein(s) having one or more acidic groups. Since the surface of the microparticles is not necessarily homogeneous, the term "subsurface" refers to the crevices and the like found on the surface of the microparticles. The bound microparticles provide a means for the controlled release of a peptide(s) and/or protein(s) in a patient. To further control the release of the immobilized peptide(s) and/or protein(s), the bound microparticles can be encased individually or in groups with an absorbable polymer coating. The bound microparticles release the peptide(s) and/or protein(s) over a period of about two days to about three months in a patient, preferably about one week to about three months. The encased microparticles release the peptide(s) and/or protein(s) over a period of about three days to six months in a patient, preferably about two weeks to five months.

A microparticle can be made of a lactide based polymer or a solid semi-crystalline polylactone such as polyglycolide which can be formed by ring opening polymerization of acid-bearing hydroxylic initiators such as glycolic, lactic, malic, tartaric, and citric acid. A microparticle of the present invention can be synthesized according to the following procedure. In a reaction vessel are mixed a lactide based monomer and/or a lactone such as glycolide and an acid initiator such as tartaric acid, malic acid or citric acid. The reaction vessel is warmed to about 35–45° C., preferably 40° C. and put under vacuum for about 20–60 minutes, preferably 30 minutes. The temperature of the reaction vessel is raised to about 105–115° C., preferably 110° C. Once this temperature is reached the vessel is placed under an atmosphere of oxygen-free nitrogen, and the mixture is stirred. Once the mixture melts, a catalytic amount of an organometallic catalyst suitable for ring opening polymerization, such as stannous 2-ethyl-hexanoate solution in a non-protic solvent, such as toluene is added. A vacuum is reapplied for about 30–90 seconds to remove toluene without significant removal of monomer. The temperature of the mixture is raised to about 115–125° C., preferably 120° C. for about 5–10 minutes before further raising it to about 145–150° C. It was kept at this temperature for about 3–5 hours, preferably 4 hours, under constant mechanical stirring, if possible.

The resulting polymer is micronized by initially grinding it using a Knife-grinder. The polymer is then micronized in an Aljet Micronizer using a pressurized dry nitrogen stream. The mean particle diameter size is analyzed in a Malvern Mastersizer/E using a volume distribution model and 200/5 cS silicone oil as dispersant.

The polymer is purified and the sodium salt thereof is formed first by dispersing the micronized polymer in acetone and placing it in a sonicator, preferably for about 30 minutes. During this time the dispersion was also homogenized at about 8,000–24,000 rpm, preferably 9,500 rpm, using a homogenizer. After this sonication/homogenization step the dispersion is centrifuged at about 3,000–7,000 rpm, preferably 5,000 rpm _preferably for about 30 minutes in a centrifuge. The supernatant is discarded, the centrifuge cakes re-suspended in fresh acetone, and the sonication/homogenization step repeated. Once the second centrifugation is complete, the supernatant is discarded and the cakes were re-suspended in deionized water. One final sonication/homogenization step is then carried out to remove any remaining acetone and the dispersion is once again centrifuged at about 5,000 rpm for about 30 minutes.

The centrifuge cakes are re-suspended in fresh deionized water and the pH of the dispersion is monitored. Sufficient volumes of a weak base such as 0.2M sodium carbonate solution are added with stirring to raise the pH to between about pH 8 and about pH 9. The dispersions are allowed to stir for about 30 minutes before being vacuum-filtered over filter paper. The filter cakes are rinsed with further deionized water, frozen, and lyophilized.

Purification is monitored by differential scanning calorimetry (DSC) with a heating rate of about 5° C./min. to 15° C./min., preferably 10° C./min.

An anion-exchanger microparticle is obtained by taking the cation-exchanger microparticles and incubating it in hot dilute solution (¯80° C. –100° C.) of a diamine, it is preferred that the amines can be both a primary amine or both a secondary amine or a mixture of a primary and a secondary amine, of known concentration in dioxane or toluene under an inert gas such as argon. The concentration of the diamine in dioxane or toluene is determined by acidimetry. When the reaction practically ceases to take place, the amidated microparticles are separated by filtration, rinsed with dioxane or toluene, and dried under reduced pressure.

A peptide(s) and/or protein(s) can be immobilized on a microparticle according to the following method. The sodium salt of a microparticle is dispersed in solutions containing the cationic form of a peptide(s) and/or protein(s) dissolved in water. The dispersions are incubated at room temperature with stirring for about 2 hours before filtering out the bound microparticles. The filter cakes are rinsed with further deionized water, frozen, and lyophilized. Samples are then analyzed for nitrogen by elemental analysis to determine the amount of the peptide(s) and/or protein(s) immobilized.

The size of a microparticle plays a role in the amount of a peptide and/or protein that a microparticle of the instant invention can immobilize. The smaller the size of a microparticle, the more surface area a mass of microparticles possess and, thus, the more peptide and/or protein can be immobilized per unit mass of microparticles. Size reduction of the microparticles to micron or sub-micron dimensions can be achieved as described above. The diameter of the microparticles can range in size from about 0.5 $\mu$m to 100 $\mu$m, preferably 10 m to 80 $\mu$m and more preferably 20 $\mu$m to 70 $\mu$m.

The absorbable encasing polymer can be a crystalline or non-crystalline lactide/glycolide copolymer, amorphous l-lactide/d,l-lactide co-polymer, caprolactone/glycolide copolymer or trimethylene carbonate/glycolide copolymer, that is soluble in conventional organic solvents, such as chloroform, methylene chloride, acetone, acetonitrile, ethyl acetate, and ethyl formate. Non-solvents of such an absorbable encasing polymer include water, aqueous or non-aqueous, low boiling temperature alcohols and supercritical fluids. The absorbable encasing polymers can be synthesized by catalyzing ring-opening polymerization of cyclic or heterocyclic monomers such as $\epsilon$-caprolactone, p-dioxanone, trimethylene carbonate, 1,5-dioxepan-2-one or 1,4-dioxepan-2-one or mixtures thereof in the presence of a chain initiator, such as a hydroxylic compounds, such as propanediol.

The encasing of the bound microparticles can be achieved by phase separation of an emulsion. An alternate encasing method entails the use of an ultrasonic atomizer where a dispersion of the bound microparticles in an absorbable encasing polymer solution is introduced as micro-droplets into a cooled non-solvent medium. Bound microparticles are encased with an absorbable encasing copolymer of lactide and glycolide using traditional microencapsulation or coating techniques of solid particles such as the emulsion evaporation method described by H. Demian and S. W. Shalaby for encapsulating barium sulfate microparticles as disclosed in U.S. Patent application U.S. Ser. No. 08/467, 361, the contents of which are incorporated herein by reference, or by coagulation of solid microparticles encased in a polymer solution and delivered through an ultrasonic atomizer (nebulizer) into a liquid medium that is a non-solvent for the encasing polymer, but where the liquid medium non-solvent is capable of extracting the solvent of the encasing polymer solution about the encased solid microparticles. Depending on the concentration of the polymer solution for encasing the microparticles, the number of the original bound microparticles in the encased microparticles can vary from 1 to several hundred with an average diameter of an encased microparticle ranging from 0.5 $\mu$m to 100 $\mu$m.

The following method relates to the preparation of encased peptide- and/or protein-loaded (hereinafter peptide-loaded) cation exchangers by nebulization. The encasing copolymer of interest is dissolved in a solvent, such as either acetonitrile, ethyl acetate or ethyl formate at a concentration of between 10 and 30% (W/W). A sufficient weight of this solution is used for dispersion of the peptide-loaded CE so that the weight ratio of peptide-loaded CE to encasing copolymer ranges from about 30:70 to about 80:20. Dispersion is achieved by high speed homogenization. The dispersion is fed at a flow rate of between 1 ml/min and 10 ml/min to an ultrasonic atomization nozzle with variable frequency—this frequency can be altered from 12kHz to 35kHz—higher frequency allows higher flow rates while maintaining particle characteristics. The dispersion is thus nebulized into a collecting sink made up of at least 1 to 10 times excess of isopropyl alcohol (IPA) or ethanol (compared to the volume of encasing copolymer solvent used) containing sufficient dry-ice so that the temperature of the slurry remains between –77° and –80° C. throughout the nebulization. This slurry is stirred at more than 100 rpm depending on its volume. In the case of acetonitrile as solvent, the nebulization droplets will freeze immediately on contact with the slurry. Once nebulization is complete the entire dispersion is allowed to thaw of its own accord to between 10° C. and room temperature before vacuum filtering. The filter cakes are rinsed with de-ionized water to remove excess non-solvent. The particles obtained have the appearance of smooth microspheres in the case of a predominantly d,l-lactide encasing copolymer; they appear slightly wrinkled when the encasing copolymer is mainly I-lactide based. In an alternative process, the encasing is achieved using a supercritical fluid, such as, $CO_2$ as the non-solvent.

The binding capacity of a microparticle ion-exchanger can be determined as follows. For example, for a cation-exchanger microparticle, available carboxylic groups, in a predetermined mass of the microparticles, are neutralized using cold dilute aqueous sodium carbonate solution of known normality. The neutralized microparticles are isolated by filtration and rinsed thoroughly with cold deionized water and then air dried. The solid microparticles are then incubated in dilute solution of Pilocarpine hydrochloride of known concentration so as to provide a slight excess of the basic drug over that predicted from the neutralization data. The concentration of the remaining Pilocarpine HCl in the aqueous medium is monitored for a period of time until no significant change in the base pick-up by the microparticles can be recorded. The percent of immobilized base on the microparticles is determined from the exhaustion data and then verified by elemental analysis for nitrogen.

The binding capacity of the anion-exchanger (amidated particles) is determined by (1) elemental analysis for nitrogen and (2) extent of binding to Naproxen by measuring the extent of Naproxen removed from a dilute solution using HPLC. The latter is confirmed by release of the immobilized Naproxen with a dilute sodium hydroxide solution of known concentration.

The bound microparticles or the encased microparticles of this invention can be administered to a patient via administration routes well known to those of ordinary skill in the art, such as parenteral administration or oral administration. Preferably it is administered as a powder or a suspension via intranasal route or as an inhalant through the pulmonary system. When it is administered parenterally it is preferable that it is administered as a dispersion in an isotonic aqueous medium or in a non-aqueous, absorbable gel-forming liquid polyester.

The effective dosages of bound microparticles or encased microparticles to be administered to a patient can be determined by the attending physician or veterinarian and will be dependent upon the proper dosages contemplated for the peptide(s) and/or protein(s) and the quantity of the peptide (s) and/or protein(s) immobilized on the microparticles. Such dosages will either be known or can be determined by one of ordinary skill in the art.

The preparation of gel-formers is disclosed in U.S. Pat. No. 5,612,052, the contents of which is incorporated herein by reference. Specific examples of gel formers are described below.

Preparation of 80/20 (by weight) Block Copolymers of 60/40 Trimethylene Carbonate/Glycolide and Polyethylene Glycol-400 (GF-1): A flame-dried resin kettle equipped with a mechanical stirrer and a nitrogen inlet was charged with polyethylene glycol-400 (0.299 mole, 119.5 g), stannous octoate (0.2 M in toluene, 4.700 ml, 0.946 mmole), glycolide (1.78 mole, 206.5 g) and trimethylene carbonate (2.65 mole, 270 g). The reactor was purged with argon several times and then heated to melt and then heated to and stirred at about 150° C. for about 12 hours. At the conclusion of the reaction, the temperature was lowered while maintaining fluidity and excess monomer was removed under reduced pressure. The resulting polymer was analyzed by infrared and NMR for composition and gel-permeation chromatography for molecular weight.

Preparation of 15/85 (by weight) Block Copolymer of 60/40 Trimethylene Carbonate/Glycolide and Polyethylene Glycol-400 (GF-2): The title copolymer was synthesized according to the procedure described for GF-1 but using polyethylene glycol-400 (1.063 mole, 425 g), stannous octoate (0.2 M in toluene, 1,760 ml, 0.35 mmole), glycolide (0.279 mole, 32.4 g) and trimethylene carbonate (0.418 mole, 42.6 g) and stirring for about 9 hours.

Preparation of 80/20 (by weight) Block Copolymer of 90/10 Trimethylene Carbonate/Glycolide and Polyethylene Glycol-1500 (GF-3): The title copolymer was synthesized according to the procedure described for GF-1 but using polyethylene glycol-1500 (0.267 mole, 400 g), stannous octoate (0.2 M in toluene, 1200 ml, 0.247 mmole), glycolide (0.097 mole, 11.2 g) and trimethylene carbonate (0.87 mole, 88.7 g) and stirring for about 13 hours.

The following Examples are provided to further illustrative the present invention, and should not be construed as limitations thereof:

EXAMPLE I

PREPARATION OF COMPONENT "A"

1. Preparation of 79/21 (by weight) Block Copolymer of 60/40 dl-Lactide/Glycolide and Polyethylene Glycol 400

A suitable flask was thoroughly cleaned, flame-dried, and charged dry with polyethylene glycol (MW-400; 5g, 0.0125 mole), dl-lactide (12 g, 0.083 mole), glycolide (6.4 g, 0.056 mole), stannous octoate catalyst (0.4 M in toluene; 34.7 $\mu$L, 0.014 mmole), and a magnetic stirrer under nitrogen condition. The reactor was placed in an oil bath and heated to 170° C. under a positive nitrogen pressure for 16 hours. The flask was removed and stored open in a vacuum oven. The inherent viscosity (IV) of the composition was determined using a 50 capillary viscometer (Ostwald type) at a concentration of 0.1 g/100 mL in chloroform. In a constant temperature bath set at 30° C., the IV was determined to be 0.13 dL/g. A DuPont 990 Differential Scanning Calorimeter (DSC) was used to determine glass transition ($T_g$) of the material. Approximately 4 mg of the sample was heated at 10° C./min from −50° C. in a nitrogen environment. $T_g$=−41° C.

2. Preparation of 60/40 (by weight) Block Copolymer of 60/40 dl-Lactide/Glycolide and Polyethylene Glycol 400 Interlinked with Oxalate Functionality Polyethylene glycol (MW=400; 4.1 g, 0.01 mole), dimethyl oxalate (3.1 g, 0.025 mole), and stannous octoate catalyst (0.4 M in toluene; 883 $\mu$L, 0.035 mmole) were mixed in a dry glass reactor containing a magnetic stirrer and heated to 150° C. under a nitrogen atmosphere for 4 hours. A vacuum of less than 0.1 mm Hg was applied to remove the condensate (methanol) and excess dimethyl oxalate. The reactor was then cooled to approximately 50° C. and PEG (MW=400; 8.3 g, 0.021 mole) was added. The reactants were heated to 150° C. for 3 hours before applying vacuum and cooling to room temperature. dl-Lactide (13.3 g, 0.093 mole), glycolide (7.2 g, 0.062 mole) were added under dry conditions to the reactor. The flask was heated to 150° C. under a positive nitrogen pressure for 12 hours. Next, the temperature was increased to 170° C. for 3.5 hours and vacuum was applied for 2 hours as the flask cooled to room temperature. The polymer was isolated and stored under vacuum. IV in $CHCl_3$=0.11 dL/g.

3. Preparation of 78/22 (by weight) Block Copolymer of 60/40 dl-Lactide/Glycolide and Polyethylene Glycol 400 Interlinked with Oxalate Functionality Polyethylene glycol (MW=400; 2.0 g, 0.005 mole), dimethyl oxalate (1.77 g, 0.015 mole), and stannous octoate catalyst (0.2 M in toluene; 90.5 µL, 0.036 mmole) were mixed in a dry glass reactor containing a magnetic stirrer and heated to 140° C. under a nitrogen atmosphere for 2 hours. A vacuum of less than 0.1 mm Hg was applied to remove the condensate (methanol) and excess dimethyl oxalate. The reactor was then cooled to approximately 50° and PEG (MW=400; 4.2 g, 0.011 mole) was added. The reactants were heated to 155° C. for 1 hour under slight vacuum before increasing the temperature to 160° C. for 2 hours under increased vacuum. l-Lactide (14.4 g, 0.1 mole), glycolide (7.7 g, 0.066 mole) were added under dry conditions to the reactor. The flask was heated to 150° C. under a positive nitrogen pressure for 15 hours. Next, the temperature was lowered to 130° C. and vacuum was applied. The material bubbled violently, indicating the presence of monomer. A strong vacuum was applied as the material cooled to room temperature. The final product was washed with 2-propanol at 40° C. for about 20 minutes to remove the excess monomer before drying under vacuum at room temperature.

The weight average molecular weight ($MW_w$) and polydispersity index (PDI) of the material was determined using a Waters Gel Permeation Chromatography (GPC) apparatus. The instrument consisted of a 600E control Module and Solvent Delivery System, a U6K injector, three Syragel HT linear columns in series, a 401 Differential Refractometer detector, and a 746 Data Module. Chloroform was used as the mobile phase at a flow rate of 1 mL/min. and polystyrene molecular weight standards were used to calibrate the system. $MW_w$: 5723; PDI: 2.42.

4. Preparation of 68/32 (by weight) Block Copolymer of 60/40 dl-Lactide/Glycolide and Polyethylene Glycol 400

Polyethylene glycol (MW=400; 15 g, 0.0375 mole), dl-lactide (21 g, 0.146 mole), glycolide (11.3 g, 0.097 mole), and stannous octoate catalyst (0.2M in toluene; 243 µL, 0.049 mmole) were added under dry conditions to a glass reactor containing a magnetic stirrer. The reactor was placed in an oil bath and heated to 150° C. under a positive nitrogen pressure for 1 hour, then to 160° C. for 6 hours. The flask was cooled under a vacuum of less than 0.1 mm Hg and placed in a vacuum oven. $MW_w$: 1670; PDI: 1.46.

5. Preparation of 68/32 (by weight) Block Copolymer of 60/40 dl-Lactide/Glycolide and Polyethylene Glycol 400 Interlinked with Oxalate Functionality Polyethylene glycol (MW=400; 160 g, 0.4 mole), dimethyl oxalate (47.2 g, 0.4 mole) and stannous octoate catalyst (0.2 M in toluene; 200 µL, 0.04 mmole) were mixed under a dry nitrogen environment and heated to 150° C. for 1 hour. The temperature was increased to 160° C. for 2 hours before applying a vacuum of 1 mm Hg and allowing to cool to approximately 50° C. Then, 5 g of PEG 400 were added and the reaction was continued at 160° for 0.5 hours. Finally, 15 g of the interlinked PEG were mixed with dl-lactide (21 g, 0.146 mole), glycolide (11.3 g, 0.097 mole), and stannous octoate catalyst (0.2 M in toluene; 243 ηL, 0.049 mmole were added under dry conditions to a glass reactor containing a magnetic stirrer. The reactor was heated to 150° C. under a positive nitrogen pressure for 1 hour, then to 160° C. for 6 hours. The flask was cooled under a vacuum of less than 0.1 mm Hg and stored in a vacuum oven. $MW_w$: 4713; PDI: 2.41.

6. Preparation of 73/27 (by weight) Block Copolymer of 60/40 dl-Lactide/Glycolide and Polyethylene Glycol 400

Polyethylene glycol (MW 400; 12.5 g), dl-lactide (22.5 g, 0.156 mole), glycolide (12.1 g, 0.104 mole), and stannous octoate catalyst (0.2 M in toluene 260 µL, 0.052 mmole) were added to a dry glass reactor containing a magnetic stirrer. The reactor was heated to 150° C. under a positive nitrogen pressure for 18 hours. The flask was cooled under a vacuum of less than 0. 1 mm Hg for 0.5 hours and stored in a vacuum oven. $MW_w$: 2172; PDI: 1.53.

7. Preparation of 73/27 (by weight) Block Copolymer of 60/40 dl-Lactide/Glycolide and Polyethylene Glycol 400 Interlinked with Oxalate Functionalities Interlinked PEG (12.5 g, described in Example 5), dl-lactide (22.5 g, 0.156 mole), glycolide (12.1 g, 0.104 mole), and stannous octoate catalyst (0.2 M in toluene; 260 µL, 0.052 mmole) were added to a dry glass reactor containing a magnetic stirrer. The reactor was heated to 150° C. under a positive nitrogen pressure for 18 hours. The flask was cooled under a vacuum of less than 0.1 mm Hg for 0.5 hours and stored in a vacuum oven. $MW_w$: 5723; PDI: 2.41.

8. Preparation of 68/32 (by weight) Block Copolymer of 60/40 dl-Lactide/Glycolide and Polyethylene Glycol 400 Interlinked with Oxalate Functionalities Interlinked PEG (15 g, described in Example 5), dl-lactide (21 g, 0.146 mole), glycolide (11.3 g, 0.097 mole), and stannous octoate catalyst (0.2 M in toluene; 243 µL, 0.049 mmole) were added to a dry glass reactor containing a magnetic stirrer. The reactor was heated to 150° C. under a positive nitrogen pressure for 3 hours and then 160° C. for 3 hours. The flask was cooled under a vacuum of less than 0.1 mm Hg for 0.5 hours and stored in a vacuum oven. $MW_w$: 3582; PCI: 2.08.

EXAMPLE II

PREPARATION OF COMPONENT "B"

1. Preparation of Polyglycolide (PG) Drug Carrier

Glycolic acid (0.46 g, 0.006 mole), glycolide (34.8 g, 0.30 mole), and stannous octoate catalyst (0.4 M in toluene; 150 µL, 0.06 mmole) were mixed in a dry flask equipped with a magnetic stirrer under a dry nitrogen atmosphere. The reactants were slowly heated to 170° C. (approx. 20 min.) under agitation. At this time, the reactants formed an opaque mixture and the temperature was increased again to 200° C. When the temperature reached 176° C., the material was translucent and the viscosity was very high. The flask was then removed from heat and quenched with liquid nitrogen for about 2 minutes. The glassware was broken and removed and the reactants were dropped in the liquid nitrogen to terminate the reaction completely. The resulting PG solid was dried in a vacuum oven at 35° C. overnight. Using a Wiley mill with a 60 mesh sieve, the PG was ground to a fine powder. The entrapped monomer was extracted using anhydrous acetone at 35° C. resulting in porous particles of PG.

2. Addition of Chlorhexidine Diacetate to PG Carrier

Chlorhexidine diacetate (8.7 g) was dissolved in approximately 500 mL of isopropyl alcohol in a roto-evaporator at 38° C. The extracted PG powder (25.6 g) (Example II-1) was added to the solution and the mixture was agitated for 6 hours under a slight vacuum. The temperature was increased to 40° C. and a stronger vacuum was applied to distill 2-propanol and acetic acid. When all of the 2-propanol had displaced, the temperature was decreased to 35° C. and the agitation was continued for another 2 hours. The resulting white powder was scraped from the containing flask and placed in a vacuum oven at 35° C. overnight. The powder was then mixed with mineral oil (1:2) and treated in a 3-roll mill for about 5 min. The oil was removed using heptane and the dry particles were shown to have an average diameter of 16 micron.

3. Preparation of Drug Carrier B—Polyglycolide

Same as in Example 11-1, except using the following polymerization charge and scheme:

| Charge: | Glycolide | 34.8 g (0.3 mole) |
|---|---|---|
| | Glycolic acid | 2.28 g (0.03 mole) |
| | Stannous octoate | 0.06 mmole |
| Scheme: | The polymerization charge was heated to 160° C. and maintained at that temperature with stirring for 15 minutes when the polymer crystallized. The product was cooled, isolated, broken into small pieces, and ground using a Wiley mill. | |

The ground polymer was mixed with about 2 parts mineral oil and roll-milled to achieve the desired particle size (about 5 min). The particles were isolated from the mineral oil as described in Example 10 and were shown to have an average diameter of 50 micron. The micronized polymer was then extracted with 2-propanol as described in Example II-1. Dry weight data indicated a 7% weight loss. Titration of the accessible carboxylic group of the particle reflects a value of 0.3 mmole/g.

4. Loading Carrier B with Chlorhexidine

One gram of Carrier B from Example II-3 was stirred with deionized water for 20 min., filtered, and air dried. Solid B particles were mixed with 150 mg of chlorhexidine diacetate in 80% aqueous acetone at 25° C. for 1 hour and 40° C. for 1 hour, cooled and then filtered. Analysis of the filtrate (using UV spectrophotometry) indicates that 80% of the drug is retained by the carrier.

EXAMPLE III

PREPARATION OF COMPONENT "C"

1. Preparation of 14/86 (by weight) of Block Copolymer of 60/40 dl-Lactide/Glycolide and Polyethylene Glycol 400

Polyethylene glycol (MW=400; 20 g, 0.05 mole), dl-lactide (2.12 g, 0.015 mole), glycolide (1.14 g, 0.010 mole), and stannous octoate catalyst (0.4 M in toluene; 25 μL, 0.05 mmole) were added under dry conditions to a glass rector containing a magnetic stirrer. The reactor was heated to 130° C. to melt the reactants and then increased to 170° C. to start the reaction. After 5 hours, the system was cooled and stored in a vacuum oven. $MW_w$: 503; PDI: 1.23

2. Preparation of 14/86 (by weight) of Block Copolymer of 60/40 dl-Lactide/Glycolide and Polyethylene Glycol 400 Interlinked with Oxalate Functionalities PEG 400 was interlinked with dimethyl oxalate (as described in Example 5) prior to the addition of dl-lactide and glycolide. Interlinked PEG (85 g), dl-lactide (9.0 g, 0.0625 mole), glycolide (4.83 g, 0.0417 mole), and stannous octoate catalyst (0.2 M in toluene; 105 JAL, 0.05 mmole) were added to a dry glass reactor and heated to 150° C. for 1 hours. The temperature was increased to 160° C. for 4 more hours before removing the reactants from heat and applying a vacuum of less than 0.1 mm Hg as the material cooled to room temperature. The polymer was isolated and stored under vacuum.

EXAMPLE IV

PREPARATION OF CHLORHEXIDINE (CHX) DELIVERY SYSTEM

1. Preparation of Drug Delivery System (1.0:0.09:0.31:0.01t A:B:C:CHX by weight)

Component C (1.20 g—Example III [1]) and Component B (0.40 g—Example II[2]) were added to 4.3 g of Component A (Example I[1]). The materials were mixed at slightly elevated temperatures (approximately 40° C.) to obtain a uniform distribution. Chlorhexidine (0.04* g) was added to the mixture to make a final composition consisting of 70.5% A, 6.5% B, 22% C, and 1% free drug. [* Based on the weight of diacetate salt].

2. Preparation of Drug Delivery System (1.0:0. 1:0.25:0.01. A:B:C:CHX by weight)

Component C (1.67 g—Example III[1]) and Component B (0.51 g—Example II[2]) were added to 4.77 g of Component A (Example I[3]) and mixed to obtain a uniform distribution. Chlorhexidine (0.05 g) was mixed into the system to make up the following composition by weight: 68% A, 7% B. 24% C, and 1% free drug.

EXAMPLE V

DRUG RELEASE FORMULATION

Samples of drug carrier (Component B) were loaded with chlorhexidine as described in Example II[4] were mixed with gel-former Component A from Examples I[4] and [5]. Another set of formulations were made of drug-bearing B, gel-former A, and plasticizer C (Example III[1]). All formulations were roll-milled for 1 to 3 minutes, transferred to a syringe, and into a 21 gauge needle. The formulations were then injected into water for subjective comparative assessment of their rate of gel formation texture and mechanical integrity. A rating of 1 to 5 was adapted for this evaluation with 1 being the fastest. A summary of these formulation compositions and ratings is provided in Table 1.

TABLE 1

Composition and Gel-Formation of Drug Delivery Formulations

| | Source of A | Source of B | Source of C | Gel-Formation |
|---|---|---|---|---|
| D Number | Ex. 4, % | Ex. 5, % | Ex. 12, % | Ex. 13, % | Rating |
| 17-1 | 40 | 40 | 20 | 0 | 4 |
| 17-2 | 30 | 55 | 15 | 0 | 4 |
| 17-3 | 30 | 40 | 30 | 0 | 5 |
| 17-4 | 40 | 30 | 30 | 0 | 3 |
| 17-5 | 45 | 25 | 30 | 0 | 3 |
| 17-6 | 40 | 20 | 40 | 0 | 3 |
| 17-7 | 0 | 50 | 30 | 20 | 1 |
| 17-8 | 30 | 40 | 20 | 10 | 2 |

EXAMPLE VI

Preparation of 80/20 (by weight) Block Copolymers of 60/40 Trimethylene Carbonate/Glycolide and Polyethylene Glycol-400 (GF-1)

A flame-dried resin kettle equipped with a mechanical stirrer and a nitrogen inlet was charged with polyethylene glycol-400 (0.299 mole, 119.5 g), stannous octoate (0.2 M in toluene, 4.700 ml, 0.946 mmole), glycolide (1.78 mole, 206.5 g) and trimethylene carbonate (2.65 mole, 270 g). The reactor was purged with argon several times and then heated to melt and then heated to and stirred at 150° C. for 12 hours. At the conclusion of the reaction, the temperature was lowered while maintaining fluidity and excess monomer was removed under reduced pressure. The resulting polymer was analyzed by infrared and NMR for composition and gel-permeation chromatography for molecular weight.

EXAMPLE VI

Preparation of 15/85 (by weight) Block Copolymer of 60/40 Trimethylene Carbonate/Glycolide and Polyethylene Glycol-400 (GF-2)

A flame-dried resin kettle equipped with a mechanical stirrer and a nitrogen inlet was charged with polyethylene glycol-400 (1.063 mole, 425 g), stannous octoate (0.2 M in toluene, 1,760 ml, 0.35 mmole), glycolide (0.279 mole, 32.4 g) and trimethylene carbonate (0.418 mole, 42.6 g). The reactor was purged with argon several times and then heated to melt and then heated to and stirred at 150° C. for 9 hours. At the conclusion of the reaction, the temperature was lowered while maintaining fluidity and excess monomer was removed under reduced pressure. The resulting polymer was analyzed by infrared and NMR for composition and gel-permeation chromatography for molecular weight.

EXAMPLE VIII
Preparation of 80/20 (by weight) Block Copolymer of 90/10 Trimethylene Carbonate/Glycolide and Polyethylene Glycol-1500 (GF-3)

A flame-dried resin kettle equipped with a mechanical stirrer and a nitrogen inlet was charged with polyethylene glycol-1500 (0.267 mole, 400 g), stannous octoate (0.2 M in toluene, 1200 ml, 0.247 mmole), glycolide (0.097 mole, 11.2 g) and trimethylene carbonate (0.87 mole, 88.7 g). The reactor was purged with argon several times and then heated to melt and then heated to and stirred at 150° C. for 13 hours. At the conclusion of the reaction, the temperature was lowered while maintaining fluidity and excess monomer was removed under reduced pressure. The resulting polymer was analyzed by infrared and NMR for composition and gel-permeation chromatography for molecular weight.

EXAMPLE IX
Preparation of Microparticulate Cation-Exchanger of Glycolide and Citric Acid Copolymer (CE-1)

A flame-dried resin kettle equipped with a mechanical stirrer and an argon inlet was charged with glycolide (2.586 mole, 300 g), anhydrous citric acid (0.172 mole, 33 g), and stannous octoate (0.2 M in toluene, 862 ml, 0.172 mmole). The polymerization reactor and its contents were purged with dry argon several times. After melting the polymerization charge, the reactants were heated and stirred at 160° C. until the polymer started to precipitate from the melt. Shortly after partial precipitation, the stirring was terminated and the reaction was continued at 160° C. for 2 hours. At the conclusion of the polymerization, the temperature was lowered below 120° C. and excess monomer was removed under reduced pressure. The composition of the isolated polymer was verified using infrared and NMR spectroscopy. Differential Scanning Calorimetry was used to determine the polymer melting temperature (Tm=205° C.). The solid polymer was ground to achieve average particle diameter of about 125 m using a Wiley mill. Further reduction of the particle size to 5–10 m diameter was achieved using a jet-mill receiving pressurized dry nitrogen. The resulting microparticles were rinsed with acetone to remove trace amounts of monomer and low molecular weight oligomers. The product was then dried under reduced pressure at 40° C. until used. The average diameter of the dry microparticle was determined using a particle size analyzer.

EXAMPLE X
Preparation of Microparticulate Cation-Exchanger of Glycolide/Malic Acid Copolymer (CE-2)

A flame-dried resin kettle equipped with a mechanical stirrer and an argon inlet was charged with glycolide (2.586 mole, 300 g), anhydrous malic acid (0.172 mole, 23 g), and stannous octoate (0.2 M in toluene, 862 ml, 0.172 m mole). The polymerization reactor and its contents were purged with dry argon several times. After melting the polymerization charge, the reactants were heated to and stirred at 160° C. until the polymer started to precipitate from the melt. Shortly after partial precipitation, the stirring was terminated and the reaction was continued at 160° C. for 2 hours. At the conclusion of the polymerization, the temperature was lowered below 120° C. and excess monomer was removed under reduced pressure. The composition of the isolated polymer was verified using infrared and NMR spectroscopy. Differential Scanning Calorimetry was used to determine the polymer melting temperature (Tm=206° C.). The solid polymer was ground to achieve average particle diameter of about 125 $\mu$m using a Wiley mill. Further reduction of the particle size to 5–10 $\mu$m diameter was achieved using a jet-mill receiving pressurized dry nitrogen. The resulting microparticles were rinsed with acetone to remove trace monomer and low molecular weight oligomers. The product was then dried under reduced pressure at 40° C. until used. The average diameter of the dry microparticle was determined using a particle size analyzer.

EXAMPLE XI
Preparation of Microparticulate Cation-Exchanger of Glycolide/Tartaric Acid Copolymer (CE-3)

A flame-dried resin kettle equipped with a mechanical stirrer and an argon inlet was charged with glycolide (2.586 mole, 300 g), anhydrous tartaric acid (0.172 mole, 26.8 g), and stannous octoate (0.2 M in toluene, 862 ml, 0.0172 mmole). The polymerization reactor and its contents were purged with dry argon several times. After melting the polymerization charge, the reactants were heated to and stirred at 160° C. until the polymer started to precipitate from the melt. Shortly after partial precipitation, the stirring was terminated and the reaction was continued at 160° C. for 2 hours. At the conclusion of the polymerization, the temperature was lowered below 120° C. and excess monomer was removed under reduced pressure. The composition of the isolated polymer was verified using infrared and NMR spectroscopy. Differential Scanning Calorimetry was used to determine the polymer melting temperature (Tm=204° C.). The solid polymer was ground to achieve average particle diameter of about 125 $\mu$m using a Wiley mill. Further reduction of the particle size to 5–10 m diameter was achieved using a jet-mill receiving pressurized dry nitrogen. The resulting microparticles were rinsed with acetone to remove trace amounts of monomer and low molecular weight oligomers. The product was then dried under reduced pressure at 40° C. until used. The average diameter of the dry microparticle was determined using a particle size analyzer.

EXAMPLE XII
Determination of the Binding Capacity of the Cation-Exchanger

The binding capacity of the microparticulate cation-exchanger was determined as follows. Available carboxylic groups, in a predetermined mass of the microparticulates, were neutralized using cold dilute aqueous sodium carbonate solution of known normality. The neutralized microparticles were isolated by filtration and rinsed thoroughly with cold deionized water and then air dried. The solid particles were then incubated in dilute solution of pilocarpine hydrochloride of known concentration so as to provide a slight excess of the basic drug over that predicted from the neutralization data. The concentration of the remaining pilocarpine salt in the aqueous medium was monitored for a period of time until no significant change in the base pick-up by the microparticulate could be recorded. The percent of immobilized base on the microparticulate was determined from the exhaustion data and then verified by elemental analysis for nitrogen.

EXAMPLE XIII

Preparation of Polyglycolide-based Microparticulate Anion-Exchanger (AE-1)

The preparation of the anion-exchanger is achieved in two steps. First, low molecular weight polyglycolide is prepared using a similar polymerization scheme as in Example IX, but using the following polymerization charge: glycolide (1 mole, 116 g), 1,3 propanediol as an initiator (30 mmole, 2.22 g), and stannous octoate (0.03 mmole). The size reduction and purification of the polymer are then conducted as described in Example IX. In the second step, the practically non-ionic microparticles are incubated in hot dilute solution (~80° C.) of hexanediamine of known concentration in dioxane under argon for 2–4 hours. The concentration of the diamine in dioxane is determined by acidimetry. When the reaction practically ceases to take place, the aminated microparticles are separated by filtration, rinsed with dioxane, and dried under reduced pressure. The binding capacity of the anion-exchanger (aminated particles) is determined by (1) elemental analysis for nitrogen and (2) extent of binding to naproxin by measuring the extent of drug removed from a dilute solution using HPLC. The latter is confirmed by release of the immobilized naproxin with a dilute sodium hydroxide solution of known concentration.

EXAMPLE XIV

Binding of Basic Organic Drug to Cation-Exchangers

Typical examples of the basic organic drugs that are available as salts of organic or inorganic acid include doxycycline HCl, gentamicin sulfate and pilocarpine HCl. In typical experiments, the aforementioned drugs are bound to the cation-exchangers of Examples IX, X, and XI following a similar scheme as that described in Example XII for determining the binding capacity of the cation-exchangers to pilocarpine. Table II depicts the content of three drugs binding to different cation-exchangers.

TABLE II

| Cation-Exchanger | Binding of Basic Organic Drugs Drug, % | | |
|---|---|---|---|
| | Pilocarpine | Gentamicin | Doxycycline |
| Example IX | 11 | 14 | 13 |
| Example X | 8 | 10 | 10 |
| Example XI | 6 | 8 | 8 |

EXAMPLE XV

Binding Acidic Organic Drugs to Anion-Exchangers

Typical examples of acidic organic drugs that are available as sodium salt are ganciclovir, naproxin, and ibuprofen. In typical experiments, the aforementioned drugs are bound to the anion-exchanger of Example XIII following a similar scheme to that used in the same example describing the binding of naproxin. Table III illustrates the content of drugs binding to the anion-exchanger of Example XIII.

TABLE III

| | Binding of Acidic Organic Drugs Drug Type | | |
|---|---|---|---|
| | Ganciclovir | Naproxin | Ibuprofen |
| % Drug | 6 | 11 | 8 |

EXAMPLE XVI

Binding Insulin to Cation-Exchangers

In a typical run, bovine insulin is treated with dilute hydrochloric acid, of known normality, to neutralize the basic amino acid sequences. The insulin solution is then incubated with cation-exchangers of Examples IX and X. A similar scheme to those described in Example XIV is used. The percent of insulin binding to the acidic surface is found to be 18 and 12% for cation-exchangers of Examples IX and X, respectively.

EXAMPLE XVII

Encasing of Microparticulate Ion-Exchangers Having Bound Active Agents with Absorbable Polymers Typical examples of the cation- and anion exchangers to which one or more active agents is bound, as described in Examples XII to XVI, are coated with an absorbable copolymer of lactide and glycolide using traditional microencapsulation or coating techniques of solid particles such as (1) the emulsion evaporation method described by H. Demian and S. W. Shalaby for encapsulating barium sulfate microparticles as disclosed in U.S. patent application U.S. Ser. No. 08/467,361, filed Jun. 6, 1995; and (2) coagulation of solid microparticles encased in a polymer solution and delivered through an ultrasonic atomizer (nebulizer) into a liquid medium that is a non-solvent for the polymer, but capable of extracting the solvent (of the polymer solution) about the encased solid microparticles. Depending on the concentration of the polymer solution for encasing the microparticles, the number of the original particles in the encased form can vary from 1 to several hundred with average diameter of encased microparticles ranging from a few microns to 100 m.

An alternative method to prepare encased micorparticles having a diameter of 15 to 50$\mu$ entails the use of supercritical fluid, such as liquid carbon dioxide as the non-solvent for the atomized system used above for nebulization.

EXAMPLE XVIII

Preparation of Doxycycline (DC) Controlled Delivery Systems

1. Preparation of Formulation F-1, Having DC and CE-3 in GF-1 and GF-2

Doxycycline hydrochloride (14 g) and cation-exchanger CE-3 of Example XI (24 g) are mixed with a mixture of gel-former GF-1 of Example VI (45 g) and GF-2 of Example VII (17 g) at about 40° C. under a dry inert atmosphere, to achieve uniform distribution of all components.

2. Preparation of Formulation F-2 Having DC and CE-3 in GF-2 and GF-3

Doxycycline hydrochloride (14 g) and cation-exchanger CE-3 of Example XI (45 g) are mixed with GF-3 of Example VIII (17 g) at about 40° C. under a dry inert atmosphere, to achieve uniform distribution of all components.

3. Preparation of formulation F-3 Having Encased DC-bearing CE-1 in a Mixture of GF-1 and GF-2

Doxycycline-bound to CE-1 prepared according to the method of example XIV and coated with 90/10 lactide/glycolide copolymer (PLG-1 made at Poly-Med following a standard ring-opening polymerization scheme) according to the method of Example XVII to produce microparticulates having an average diameter of 75 m and comprising DC, CE-1, and PLG-1 in a ration of 1.5:6.5:2. The coated drug-loaded microparticles (30 g), and doxycycline hydrochloride (8 g) are mixed with a mixture of gel-former GF-1 of Example VI (40 g) and GF-2 of Example VII (12 g) at about 40° C. under a dry inert atmosphere, to achieve uniform distribution of all components.

4. Preparation of Formulation F-4 Having Encased and Unencased Doxycycline Hydrochloride in GF-1 and GF-2

Microparticles of doxycycline hydrochloride having an average diameter of 20 m are encased in a 90/10 lactide/glycolide copolymer solution in methylene chloride (PLG-1, made at Poly-Med using a standard ring-opening polymerization scheme) using an ultrasonic atomizer according to the process described in Example XVII. The resulting microparticles have an average diameter of about 50 m and consist of about 50% doxycycline hydrochloride and 50% PLG-1. The encased drug (10 g), uncoated doxycycline (7 g) are mixed with a mixture of gel-former GF-1 of Example VI (70 g) and GF-2 of Example VII (12 g) at 40° C. in an inert dry atmosphere to achieve uniform distribution of all components.

EXAMPLE XIX
Preparation of Formulation F-5 Having Encased Insulin-bearing CE-1 in a Mixture of GF-1 and GF-2

Insulin bound to CE-1 microparticles having an average diameter of about 10 m are prepared according to the method of Example XIV and encased with a 90/10 lactide/glycolide copolymer (PLG-1 made at Poly-Med following a standard ring-opening polymerization scheme) using an ultrasonic atomizer according to the method of Example XVII. The resulting microparticles have an average diameter of abut 75 m and comprising insulin, CE-1 and PLG-1 in a ration of 1.0:7.2. The encased insulin-loaded microparticles (20 g) are mixed with a mixture of gel-former GF-1 of Example VI (60 g) and gel-former GF-2 of Example VII (20 g) at about 37° C. under dry inert atmosphere, to achieve uniform distribution of all components.

EXAMPLE XX
Preparation of Formulation F-6 Having Encased Gentamicin-bearing CE-1 and Gentamicin Sulfate in a Mixture of GF-1 and GF-2

Gentamicin bound to CE-1 microparticles having an average diameter of 10 m are prepared according to the method of Example XIV and encased with a 90/10 lactide/glycolide copolymer (PLG-1 made at Poly-Med following a standard ring-opening polymerization scheme) using an ultrasonic atomizer (nebulizer) according to the method of Example XVII. The resulting microparticles have an average diameter of 75 m and comprising gentamicin, CE-1, and PLG-1 in a ratio of 1:7:2. The encased microparticles (20 g) and gentamicin sulfate (3 g) are mixed with a mixture of gel-former GF-1 of Example VI (45 g) and gel-former GF-2 of Example VII (32 g) at about 40° C. to achieve uniform distribution of all components.

EXAMPLE XXI
Comparative Evaluation of the In Vitro Release Profile of Drug Formulations An aliquot of a gel-forming formulation having a mass of 50 mg was placed in a continuous flow-cell system where a buffered phosphate solution at pH 7.2 and 37° C. flow tangentially along the surface of the gel-mass at a rate of about 45 ml/hr. For solid encased microparticles (no gel-former), a modification of the flow-cell is used that allows the buffer to flow across the entire mass. Samples of the buffer containing the released drug are collected at 4° C. and analyzed for the drug concentrations at 1- or 2-day intervals. The release profile of the individual formulations is determined over a period of 2 weeks. The relative cumulative percent release at 2 weeks are depicted in Table IV using a 1–10 scale where 1 and 10 represent a very slow and very fast release, respectively.

TABLE IV

Relative Release Profile of Solid and Gel-Forming Drug-Release Systems

| Formulation | | Active | Relative Release |
|---|---|---|---|
| Type[a] | From Example No. | Agent | Rate @ 2 Weeks |
| A | XVIII-1 | Doxycycline | 6 |
| A | XVIII-2 | " | 7 |
| A | XVIII-3 | " | 4 |
| A | XVIII-4 | Insulin | 5 |
| A | XIX | " | 1 |
| B | XIX[b] | Gentamicin | 2 |
| A | XX | " | 5 |

[a]A = Coated solid microparticles; B = Gel-forming system
[b]Same as XIX, but instead, without the liquid gel-formers.

EXAMPLE XXII
Preparation of a Hemostatic Adhesive Formulation

1. Preparation of a Hemostatic Adhesive Formulation (F-7) from GF-1 and Methoxypropyl Cyanoacrylate Gel-former GF-1 of Example VI (1.5 g) was dissolved in methoxypropyl cyanoacrylate (8.5 g, obtained from National Starch) under dry inert atmosphere at about 40° C.

2. Preparation of a Hemostatic Adhesive Formulation (F-8) from Acid-tipped GF-1 and Methoxypropyl Cyanoacrylate Gel-Former GF-1 of Example VI was heated in a dry inert atmosphere with a stoichiometric amount of glutaric anhydride at 100° C. for 30 min. to acylate the hydroxyl endgroups of the polymer. An aliquot of the acylated GF-1 (1.5 g) was dissolved in methoxypropyl cyanoacrylate (8.5 g, obtained from National Starch) under dry inert atmosphere at 40° C.

3. Preparation of Hemostatic Adhesive Formulation (F-9) from GF-1 GF-2 and Ferric Chloride Anhydrous ferric chloride (1.0 g) was dissolved in a mixture of gel-former GF-1 of Example VI (7 g) and gel-former GF-2 of Example VII (3 g) in a dry inert atmosphere at about 40° C. to achieve uniform distribution of all components.

EXAMPLE XXIII
In Vivo Evaluation of Hemostatic Adhesive Formulation

The hemostatic adhesive formulations (F-7 to F-9) of Example XVI and a mixture of GF-1 and GF-2 (at 70/30 ratio) are evaluated in a rabbit animal model to determine their effectiveness in stopping bleeding and formation of a high-integrity barrier film. This is determined primarily in terms of time to achieve homeostasis, need to repeat the application of the agent and flexibility and mechanical integrity of the barrier. Using a rabbit animal model, two sites are used, namely lacerated liver and punctured vena cava. The overall rating of the different agents are given below on a scale of 1 to 10, with 10 being the best performance.

| Formulation | Rating |
| --- | --- |
| GF-1 and GF-2 | 2 |
| F-9 | 8 |
| F-8 | 10 |
| F-7 | 10 |

EXAMPLE XXIV

In Vivo Evaluation of Gel-forming Formulation for Accelerated Wound Healing

A mixture of gel-formers GF-1 (8.5 g) and GF-2 (1.5 g) is evaluated for its efficacy in promoting wound healing using a hairless rat as an animal model. Using an incisional wound with 10 metallic staples as a control and 4 staples along with the gel-former indicate that the latter system is at least 30% more effective in regaining the original wound strength and minimizes scar formation at a 3-week period. Applying the gel-formulation to a second-degree skin burn wound reflects discernible improvement on area reduction and healing rate as compared to a control.

EXAMPLE XXV

Preparation and Evaluation of Intravitreal Formulation of Ganciclovir

Ganciclovir sodium (1.0 g), an antiviral drug for treating megalovirus retinitis, is mixed with a mixture of gel-formers GF-1L (4.5 g) and GF-2L (4.5 g) (the dl-lactide-based analogs of GF-1 and GF-2 of Examples I and II, respectively—i.e., dl-lactide was used instead of trimethylene carbonate in preparing the copolymer), in an inert dry atmosphere at about 40° C. to achieve uniform distribution of all components. The in vitro release profile of the gel-forming formulation was evaluated using the continuous flow-cell system of Example XXI. The drug concentration was determined using HPLC. The results indicate that the system continues to release for at least 2 weeks. Using a small gauge needle syringe, the formulation was easily administered intravitreally into the rabbit eye. No adverse reaction could be detected during the study period.

EXAMPLE XXVI

Preparation and Evaluation of Intravitreal Formulation of Cyclosporin (F-11)

Cyclosporin (0.5 g), an immunosuppressant, is mixed with a mixture of gel-former GF-IL (4.75 g) and GF-2L (4.75 g) as described for ganciclovir in Example XXV. The in vitro release profile was determined using the continuous flow cell system of Example XXI. The drug concentration was determined using HPLC. The results indicate that the system releases less than 20% over a 4-week period. Using a small gauge needle syringe, the formulation was easily administered intravitreally into the rabbit eye. A discernible amount of the drug was detected in the remaining polymer in the vitreous humor at 4 weeks post-administration.

EXAMPLE XXVII

Preparation and Evaluation of Vancomycin Formulation

1. Preparation of Vancomycin Formulation (F-12) with CE-3 in GF-1 and GF-2

Vancomycin hydrochloride (1.0 g) and cation-exchanger CE-3 from Example XI are mixed with a mixture of gel-formers GF-1 (9.0 g) and GF-2 (1.0) from Examples VI and VII, respectively, at 40° C. under a dry inert atmosphere to achieve uniform distribution of all components.

2. Preparation of Vancomycin Formulation (F-13) with CE-G, GF-1L and GF-2L

The cation-exchanger CE-G was made following the same procedure used for CE-2 with the exception of substituting glycolic acid for malic acid as the initiator. Gel-formers GF-IL and GF-2L are the lactide analogs of GF-1 and GF-2 that were made using dl-lactide instead of trimethylene carbonate. The formulation was made as described for F-12 in Example XXVII-1.

3. In Vitro Evaluation of the Controlled Release of F-12 and F-13

The in vitro release profile of both formulation was conducted using the continuous-flow cell system described in Example XXI. The drug concentration at different periods was determined using HPLC. The results indicate that about 50 and 90% of vancomycin is released at 2 weeks for formulation F-12 and F-13, respectively.

4. In Vivo Evaluation of the Controlled Release of Formulation F-13

In pursuing this study, goat was used as the animal model; the tibia was exposed surgically and incisions were made in the periosteum. After raising the periosteum temporarily, F-12 (3.5 g) was extruded about the incision. The wound was then closed and the drug concentration in the animal blood serum was monitored during a 1-week period using fluorescence polarization immunoassay (FPI). At the conclusion of the 4-week period, the animal was euthanized and a segment of the tibia and surrounding tissue above and below the administration site were removed and analyzed for vancomycin using FPI. The results indicate that (1) only a small concentration of vancomycin, well below the toxic level, was present in blood during the first week, and was undetectable thereafter; (2) a discernible amount of the drug was present in bone at least for the first 2 weeks; and (3) discernible amounts of the drug were present in soft tissue about the administration site at the 4-week period.

EXAMPLE XXVIII

Preparation and Evaluation of Gentamicin Formulation (F-14) with CE-G. GF-1L. and GF-2L This formulation was prepared as discussed in example XXVII-2 with the exception of substituting vancomycin hydrochloride with gentamicin sulfate. In vitro evaluation of the release profile was conducted as described for vancomycin in Example XXVII-3. The results indicate that gentamicin continued to release beyond a 4-week period.

EXAMPLE XXIX

Preparation and Evaluation of Ricin A-Chain Vaccine Formulations (F-15 and F-16) Containing CE-RG and GF-3L 1. Preparation of Formulation F-15

A gel-former (GF-3L) based on a 62:19:19 mixture of three copolymers of polyethylene glycol-400 and 60/40 dl-lactide/glycolide copolymers with a PEG-polyester ratio of 20/80, 30/70, and 85/15, respectively, was used as the liquid carrier. Copolymers were made according to procedures described in U.S. Pat. No. 5,612,052, hereby incorporated by reference. To prepare Formulation F-15, ricin A-chain (20 μg) was immobilized (from an aqueous solution, followed by lyophilization) on the surface of cation-exchanger CE-G (10 mg) (prepared as described in Example XXVII-2) and then dispersed in GF-3L (190 μl), under aseptic dry conditions.

2. Preparation of Formulation F-16

In this example, formulation F-16 is prepared in the same manner as F-15 described in Example XXIX-1 with the exception of encasing the cation-exchanger, having the immobilized vaccine, with PLG-1 as described in Example XVIII-3, except that the mixing to the components is conducted at 25° C.

3. In Vivo Evaluation of Formulation F-15

To evaluate the antibody response to F-15, the formulation was injected subcutaneously into mice and the animals were bled periodically over al period of 21 weeks. The mice sera were assayed using ELISA. Results indicate that due to the controlled release of the vaccine, the antibody response persisted over the entire study period.

EXAMPLE XXX

Preparation, Micronization, and Purification of Poly (glycolic acid) polymers initiated with Citric Acid (PGCA) for use as Cation Exchangers (CE)

1. 7/1 PGCA

A 500 ml glass reactor was loaded with 242.63 g of glycolide (Purac Biochem, Arkelsedijk, The Netherlands) and 57.37 g of citric acid (Aldrich, Gillingham, Dorset, U.K.). The citric acid had been further dried over silica gel (Fisher Scientific, Loughborough, Leics., U.K.) in an Abderhalden apparatus (Aldrich, St. Louis, Mo., USA). The reactor was immersed in an oil bath at about 40° C. and put under vacuum (0.04 mbar) for about 30 minutes. The bath was then lowered and it's temperature raised to about 110° C. Once this temperature was reached the reactor was placed under an atmosphere of oxygen-free nitrogen and re-immersed. The contents were stirred at about 100 rpm using a Heidolph stirrer (Heidolph Elektro GmbH, Kelheim, Germany). Once the reactor contents melted 1.09 ml of a 0.1M stannous 2-ethyl-hexanoate solution (Sigma, St. Louis, Mo., USA) in toluene (Riedel de-Haen, Seelze, Germany) was added (stoichiometric ratio of 50 ppm). A vacuum was reapplied via a liquid nitrogen trap for about 30 seconds to remove toluene without significant removal of monomer. The oil bath temperature was then raised to about 120° C. for about 5 minutes before further raising it to about 150° C. It was kept at this temperature for about 4 hours under constant mechanical stirring of about 100 rpm. The title polymer was obtained.

2. 10/1 PGCA

The title polymer was obtained by following the procedure of Example Ia, but using 257.40 g of glycolide, 42.60 g of citric acid and 1.10 ml of a 0.1M stannous 2-ethylhexanoate solution in toluene (stoichiometric ratio of 50 ppm).

3. 15/1 PGCA And 15/1 PGCA

A flame-dried resin kettle equipped with a mechanical stirrer and an argon inlet was charged with glycolide (2.586 mole, 300 g), anhydrous citric acid (0.172 mole, 33 g), and stannous octoate (0.2 M in toluene, 862 ml, 0.172 mmole). The polymerization reactor and its contents were purged with dry argon several times. After melting the polymerization charge, the reactants were heated and stirred at about 160° C. until the polymer started to precipitate from the melt. Shortly after partial precipitation, the stirring was terminated and the reaction was continued at about 160° C. for about 2 hours. At the conclusion of the polymerization, the temperature was lowered below 120° C. and excess monomer was removed under reduced pressure. The composition of the isolated polymer was verified using infrared and NMR spectroscopy.

4. Micronization

Each of the polymers of Examples XXX(1), (2) and (3) were ground initially using a Knife-grinder (IKA, Staufen, Germany). They were then micronized in an Aljet Micronizer (Fluid Energy Aljet, Plumsteadsville, Pa., USA) using a pressurized dry nitrogen stream. Example XXX(1) had a mean particle diameter size of 24.84 $\mu$m by analysis in a Malvern Mastersizer/E (Malvern, Worcs., U.K.) using a volume distribution model and 200/5 cS silicone oil (Dow Corning, Seneffe, Belgium) as dispersant. Examples XXX (2) and (3) had mean particle diameter sizes of 4.69 $\mu$m and 6.31 $\mu$m, respectively, after Micronization.

5. Purification/Sodium Salt Formation

Fifty gram batches of Examples XXX(1), (2), and (3) were dispersed in 2 L of acetone (Riedel de-Haen, Seelze, Germany) and placed in a sonicator (Branson Ultrasonics BV, Soest, The Netherlands) for about 30 minutes. During this time the dispersion was also homogenized at about 9,500 rpm using an Ultra-turrax T25 homogenizer (IKA, Staufen, Germany). After this sonication/homogenization step the dispersion was centrifuged at about 5,000 rpm for about 30 minutes in a Sorvall centrifuge (Sorvall, Wilmington, Del., USA). The supernatant was discarded, the centrifuge cakes re-suspended in fresh acetone, and the sonication/homogenization step repeated. Once the second centrifugation was complete, the supernatant was discarded and the cakes were re-suspended in deionized water. One final sonication/homogenization step was then carried out to remove any remaining acetone and the dispersion was once again centrifuged at about 5,000 rpm for about 30 minutes.

The centrifuge cakes were re-suspended in fresh deionized water and the pH of the dispersion was monitored. Sufficient volumes of 0.2M sodium carbonate solution were added in each case (with stirring) to raise the pH to between about pH 8 and about pH 9. The dispersions were allowed to stir for about 30 minutes before being vacuum-filtered over a Whatman no. 1 (24 cm diameter) filter paper (Whatman Intl. Ltd., Maidstone, Kent, U.K.). The filter cakes were rinsed with further deionized water, frozen, and lyophilized in an Edwards SuperModulyo Lyophilizer (Edwards, Crawley, West Sussex, U.K.).

Purification was monitored by differential scanning calorimetry (DSC) using a TA DSC912S (TA Instruments, New Castle, Del., USA) with a heating rate of 10° C./min. The DSC thermograms obtained in each case did not show any endothermic peak for monomeric glycolide but showed endotherms at 176° C., 178° C., and 180° C. for Examples I(a), I(b), and I(c), respectively.

EXAMPLE XXXI

Preparation, Micronization, and Purification of a Poly(glycolic acid) polymer initiated with Tartaric Acid (PGTA) for use as a Cation Exchanger (CE)

1. 10/1 PGTA

A 500 ml glass reactor was loaded with 264.65 g of glycolide (Purac Biochem, Arkelsedijk, The Netherlands) and 34.22 g of L-Tartaric acid (Riedel de-Haen, Seelze, Germany). The tartaric acid had been further dried over silica gel (Fisher Scientific, Loughborough, Leics., U.K.) in an Abderhalden apparatus (Aldrich, St. Louis, Mo.). The reactor was immersed in an oil bath at about 40° C. and put under vacuum (0.04 mbar) for about 30 minutes. The bath was then lowered and it's temperature raised to about 110° C. Once this temperature was reached the reactor was placed under an atmosphere of oxygen-free nitrogen and re-immersed. The contents were stirred at about 100 rpm using a Heidolph stirrer (Heidolph Elektro GmbH, Kelheim, Germany). Once the reactor contents melted 1.14 ml of a 0.1M stannous 2-ethyl-hexanoate solution (Sigma, St. Louis, Mo., USA) in toluene (Riedel de-Haen, Seelze, Germany) was added (stoichiometric ratio of 50 ppm). A vacuum was reapplied via a liquid nitrogen trap for about 30 seconds to remove toluene without significant removal of monomer. The oil bath temperature was then raised to about 120° C. for about 5 minutes before further raising it to about 150° C. It was kept at this temperature for about 4 hours under constant mechanical stirring of about 100 rpm. The title polymer was obtained and processed further as shown hereinafter.

2. Micronization

Example XXXI(1) was ground initially using a Knife-grinder (IKA, Staufen, Germany). It was then micronized in an Aljet Micronizer (Fluid Energy Aljet, Plumsteadsville, Pa., USA) using a pressurized dry nitrogen stream. This gave a mean particle diameter of 12.42 μm by analysis in a Malvern Mastersizer/E (Malvern, Worcs., U.K.) using a volume distribution model and 200/5 cS silicone oil (Dow Corning, Seneffe, Belgium) as dispersant.

3. Purification/Sodium Salt Formation

A 50 g batch of Example XXXI(1) was dispersed in 2 L of acetone (Riedel de-Haen) and placed in a sonicator (Branson Ultrasonics BV, Soest, The Netherlands) for about 30 minutes. During this time the dispersion was also homogenized at about 9,500 rpm using an Ultra-turrax T25 homogenizer (IKA, Staufen, Germany). After this sonication/homogenization step the dispersion was centrifuged at about 5,000 rpm for about 30 minutes in a Sorvall centrifuge (Sorvall, Wilmington, Del., USA). The supernatant was discarded, the centrifuge cakes re-suspended in fresh acetone, and the sonication/homogenization step repeated. Once the second centrifugation was complete, the supernatant was discarded and the cakes were re-suspended in deionized water. One final sonication/homogenization step was then carried out to remove any remaining acetone and the dispersion was once again centrifuged at about 5,000 rpm for about 30 minutes.

The centrifuge cakes were resuspended in fresh de-ionized water and the pH of the dispersion was monitored. A sufficient volume of 0.2M sodium carbonate solution was added to raise the pH to between about pH 8 and about pH 9. The dispersion was allowed to stir for about 30 minutes before being vacuum-filtered over a Whatman no. 1 (24 cm diameter) filter paper (Whatman Intl. Ltd., Maidstone, Kent, U.K.). The filter cake was rinsed with further deionized water, frozen, and lyophilized in an Edwards SuperModulyo Lyophilizer (Edwards, Crawley, West Sussex, U.K.).

Purification was monitored by DSC using a TA DSC912S (TA Instruments New Castle, Del., USA) with a heating rate of about 10° C./min. The DSC thermogram obtained did not show any endothermic peak for monomeric glycolide but showed an endotherm at 181° C.

4. 15/1 PGTA

The title polymer was synthesized according to the procedure described for Example XXX(3) but using glycolide (2.586 mole, 300 g), anhydrous tartaric acid (0.172 mole, 26.8 g) and stannous octoate (0.2 M in toluene, 862 ml, 0.0172 mmole). Differential Scanning Calorimetry was used to determine the polymer melting temperature (Tm=204° C.).

The solid polymer was ground to achieve average particle diameter of about 125 μm using a Wiley mill. Further reduction of the particle size to about 5–10 μm diameter was achieved using a jet-mill receiving pressurized dry nitrogen.

The resulting microparticles were rinsed with acetone to remove trace amounts of monomer and low molecular weight oligomers. The product was then dried under reduced pressure at about 40° C. until used. The average diameter of the dry microparticle was determined using a particle size analyzer.

EXAMPLE XXXII

Preparation of Poly(lactide co-glycolide) copolymers initiated with propanediol (PLGPD) for use as encasing materials 1. 75/25 P(l)LGPD A 500 ml glass reactor was loaded with 235.01 g of l-lactide(Purac Biochem, Arkelsedijk, The Netherlands), 63.09 g of glycolide (Purac Biochem, Arkelsedijk, The Netherlands) and 1.90 g of propanediol (Riedel de-haen, Seelze, Germany) and then 3.96 ml of a 0.1M stannous 2-ethyl-hexanoate solution (Sigma, St. Louis, Mo., USA) in toluene (Riedel de-haen, Seelze, Germany) was added (stoichiometric ratio of 200 ppm). After drying under vacuum for about one hour to remove the toluene, the reactor was placed under an atmosphere of oxygen-free nitrogen and immersed in an oil bath preheated at about 160° C. The reactor contents were stirred at about 100 rpm with a Heidolph stirrer (Heidolph Elektro GmbH, Kelheim, Germany). Once the contents had melted the temperature was increased to about 180° C. and maintained at this level for about 3 hours. An amorphous copolymer was obtained. The copolymer was found to have a molecular weight (MW) of about 12,500 g/mol by gel permeation chromatography (GPC) on a Waters 510 Pump, Waters 410 Differential Refractometer (Waters, Milford, Mass., USA) with light-scattering detection on a Wyatt Minidawn Light Scattering Detector (Wyatt Technology Corporation, Santa Barbara, Calif., USA).

2. 90/10 P(l)LGPD

The title product was synthesized according to the procedure of Example XXXII(1) but using 274.31 g of l-lactide, 24.55 g of glycolide, 1.14 g of propanediol and 3.89 ml of a 0.1M stannous 2-ethyl-hexanoate solution in toluene (stoichiometric ratio of 200 ppm). A crystalline copolymer was obtained. The copolymer was found to have a molecular weight of about 20,780 g/mol by GPC.

3. 90/10 P(d,l)LGPD

The title product was obtained by following the procedure of Example XXXII(1) but using 274.31 g of d,l-lactide, 24.55 g of glycolide, 1.14 g of propanediol and 3.86 ml of a 0.1M stannous 2-ethyl-hexanoate solution in toluene (stoichiometric ratio of 200 ppm). An amorphous copolymer was obtained. The copolymer was found to have a molecular weight of about 20,650 g/mol by GPC.

4. Poly(l-lactide co-d,l-lactide) copolymer initiated with propanediol (PLGPD) for use as coating material 80/20 P(lL(d,l)LPD The title product was obtained by following the procedure of Example XXXII(1) but using 239.09g of l-lactide, 59.77g of d,l-lactide (Purac Biochem, Arkelsedijk, The Netherlands) and 1.14 g of propanediol and 3.96 ml of a 0.1M stannous 2-ethyl-hexanoate solution in toluene was added (stoichiometric ratio of 200 ppm). An amorphous copolymer was obtained. The copolymer was found to have a molecular weight (Mw) of 22,320 g/mol by GPC. It showed a glassy transition at 48° C. by DSC.

5. Purification

Examples XXXII(1), (2), and (3) were each washed by nebulization of a 30% (W/W) solution in acetonitrile (Labscan, Dublin, Ireland) at 8 ml/min into deionized water cooled to about 2° C. in a 6L jacketed reactor linked to a circulation bath and stirred at about 350 rpm with a Heidolph stirrer (Heidolph Elektro GmbH, Kelheim, Germany). The solutions were fed to a Vibra-Cell VC 50 Atomization nozzle (Bioblock, Illkirch, France) using a Masterflex pump (Cole Parmer Instrument Co., Niles, Ill., USA) and nebulization was achieved using a sonication frequency of 12 kHz. The dispersions obtained were filtered over Whatman No. 1 (24 cm diameter) filter papers (Whatman Intl. Ltd., Maidstone, Kent, U.K.) and the filter cakes were rinsed with deionized water, frozen, and lyophilized in an Edwards SuperModulyo Lyophilizer (Edwards, Crawley, West Sussex, U.K.).

Purity was confirmed by DSC using a TA DSC912s (TA Instruments, New Castle, Del., USA) with a heating rate of 10° C./min which showed glass transitions ($T_g$) at 44° C., 49° C., and 45° C. for Examples V(a), V(b) and V(c), respectively.

It is understood that the Examples described herein are for purposes of illustration only and, not limitation, and that various modification and/or changes that may suggest themselves to one skilled in the art are intended to be included within the spirit of this application and the scope of the appended claims.

We claim:

1. A hydrogel-forming, self-solvating absorbable polyester copolymer capable of selective, segmental association into a compliant hydrogel mass on contact with an aqueous environment, said copolymer comprising:
    a hydrophobic polyester block X and a hydrophilic block Y, said blocks X and Y being covalently bonded together in an arrangement selected from the group consisting of X-Y-X, (X-Y)n, and branched structures thereof;
    said hydrophobic block comprising greater than 50% of the mass of said copolymer and derived front a process selected from the group consisting of ring-opening of a cyclic carbonate and step-growth polymerization of an alkylene carbonate.

2. The copolymer of claim 1, wherein said cyclic carbonate is selected from the group consisting of substituted or unsubstituted alkylene carbonate.

3. The copolymer of claim 1, wherein said step-growth polymerization forms a polyalkylene carbonate corresponding to diols having more than 3-carbon atoms in a linear sequence.

4. The copolymer of claim 2, further comprising microparticles of hydroxyproline.

5. A composition comprising:
    a hydrogel-forming, self-solvating absorbable polyester copolymer capable of selective, segmental association into a compliant hydrogel mass on contact with an aqueous environment;
    a low molecular weight component associated with said copolymer; and
    an absorbable microparticulate solid carrier associated with said copolymer and said component, said carrier having a biological active agent or mixtures of biologically active agents deposited thereon.

6. The composition of claim 5, wherein said carrier comprises surface or total bulk microporosity.

7. The composition of claim 6, wherein said surface comprises ionizable functional groups capable of producing an anionic or cationic stationary phase.

8. The composition of claim 7, wherein said anionic phase forms a complex with an immobilized biologically active agent or mixture of agents carrying one or more basic ionogenic groups.

9. The composition of claim 7, wherein said cationic stationary phase forms a complex with an immobilized biologically active agent carrying one or more acidic groups.

10. The composition of claim 8, wherein said active agent is an antibiotic.

11. The composition of claim 10, wherein said antibiotic is doxycycline.

12. The composition of claim 11, further comprising said microparticulate being encased in an absorbable polymer.

13. The composition of claim 12, wherein said microparticulate is encased in said polymer individually or in groups.

14. A composition comprising:
    a hydrogel-forming, self-solvating absorbable polyester copolymer capable of selective, segmental association into a compliant hydrogel mass on contact with an aqueous environment; and
    an absorbable microparticulate, microporus, carrier associated with said copolymer, said carrier having a biological active agent deposited thereon; and
    the surface of said carrier being anionic and complexing with said agent.

15. The composition of claim 14, wherein said micorparticulate is encased individually or in groups with an absorbable polymer.

16. A composition comprising:
    a hydrogel-forming, self-solvating absorbable polyester copolymer capable of selective, segmental association into a compliant hydrogel mass on contact with an aqueous environment; and
    an absorbable microparticulate, microporus, carrier associated with said copolymer, said carrier having a biological active agent deposited thereon; and
    the surface of said carrier being cationic and complexing with said agent.

17. The composition of claim 16, wherein said micorparticulate is encased individually or in groups with an absorbable polymer.

18. A method of treating ocular diseases or disorders in a patient suffering from such diseases comprising, placing at the site of said disease a formulation comprising a hydrogel-forming, self-solvating absorbable polyester copolymer capable of selective, segmental association into a compliant hydrogel mass on contact with an aqueous environment and a pharmaceutically acceptable carrier.

19. The method of claim 18, wherein said formulation is an intraocular injectable formulation.

20. A method of accelerating incisional wound healing and reducing scaring in a patient comprising placing at the site of said disease a formulation consisting of a hydrogel-forming, self-solvating absorbable polyester copolymer capable of selective, segmental association into a compliant hydrogel mass on contact with an aqueous environment and a pharmaceutically acceptable carrier.

21. A method for assisting the approximation of wound edges and healing in conjunction with a limited number of suture stitches, or staples in a patient suffering from such conditions, comprising placing at the site of said condition of said person the copolymer according to claim 3.

22. The composition of claim 12, wherein said polymer is a polyester.

23. The composition of claim 22, wherein said polyester is a lactide/glycolide copolymer.

24. A mixture comprising the polyester copolymer of claim 1 and an alkoxyalkyl cyanoacrylate.

25. The mixture of claim 24, wherein said alkoxyalkyl cyanoacrylate is methoxy-propyl cyanoacrylate.

26. The mixture as in claim 25, wherein said alkoxy cyanoacrylate comprises 5 to 50 percent by weight of the mixture.

27. The mixture of claim 26, wherein said mixture facilitates wound repair.

28. The mixture of claim 26, wherein said mixture is a hemostat agent.

29. The composition of claim 12, wherein said carrier is dispersed in a sterile aqueous formulation for parenteral administration.

30. The composition of claim 5, wherein said active agent is a polypeptide.

31. The composition of claim 29, wherein said active agent is a polypeptide.

32. The copolymer of claim 2, wherein said cyclic carbonate is trimethylene carbonate.

33. The composition of claim 5, wherein said active agent is a protein.

34. The composition of claim 33, wherein said protein is selected from the group consisting of insulin, interferon, growth hormone, erythropoitin and ricin A-chain.

35. The composition of claim 29, wherein said active agent is a protein.

36. The composition of claim 35, wherein said protein is selected from the group consisting of insulin, interferon, growth hormone, erythropoitin and ricin A-chain.

37. The copolymer of claim 1 further comprising a hydroxy terminal group acylated with a cyclic anhydride.

38. The copolymer of claim 37, wherein said cyclic anhydride is glutaric anhydride.

39. The copolymer of claim 2, further comprising microparticles of hydroxyproline encased in an absorbable polyester.

40. The copolymer of claim 4, further comprising microparticles of the free acid of naproxin sodium.

41. A method for preventing post-surgical adhesion in a person suffering from such a condition comprising placing at the site of the condition the copolymer according to claims 4, 39 or 40.

42. A mixture comprising the polyester copolymer of claim 1 and anhydrous ferric chloride.

43. A method for achieving homeostasis or temporary blocking of blood vessels and biological conduits in a person suffering from such a condition comprising placing at the site of the condition the mixture according to claims 26, 27 or 42.

44. A method for sealing damaged soft tissue in a person suffering from such a condition comprising placing at the site of the condition the formulation according to claims 27 or 42.

45. The copolymer of claim 2, wherein said copolymer further comprises an absorbable microparticulate solid carrier associated with said copolymer, said carrier having a biological active agent or mixtures of biologically active agents deposited thereon.

46. The copolymer of claim 45, wherein said active agent is doxycycline encased in an absorbable polymer.

47. The copolymer of claim 46, wherein said polymer is a lactide/glycolide copolymer.

48. A method for treating periodontitis in a person suffering from such a condition comprising placing at the site of the condition the formulation according to claim 46.

49. A method for treating osteomyelitis in a person suffering from such a condition comprising placing at the site of the condition the formulation according to Examples XX and XXVII.

50. A method for accelerating wound healing in a person suffering from such a condition comprising placing at the site of the condition the formulation according to claim 1.

51. The composition of claim 5, wherein said active agent is a vaccine.

52. A process for making an encased microparticle comprising the step of encasing a bound microparticle with an absorbable polymer.

53. The process according to claim 52, wherein a dispersion of said bound microparticle in a solution comprising said absorbable polymer and a solvent is dropped onto a pre-cooled organic medium.

54. The process according to claim 53, wherein said medium comprises isopropyl alcohol and carbon dioxide.

55. The process according to claim 53, wherein said medium comprises a supercritical fluid as a non-solvent.

* * * * *